(12) United States Patent
Kannan et al.

(10) Patent No.: US 10,426,842 B2
(45) Date of Patent: Oct. 1, 2019

(54) TARGETED NANOPARTICLE CONJUGATE AND METHOD FOR CO-DELIVERY OF SIRNA AND DRUG

(71) Applicant: The Curators of the University of Missouri, Columbia, MO (US)

(72) Inventors: Raghuraman Kannan, Columbia, MO (US); Srikar Raman, Columbia, MO (US); Anandhi Upendran, Columbia, MO (US); Dhananjay Suresh, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/743,892

(22) PCT Filed: Jul. 14, 2016

(86) PCT No.: PCT/US2016/042191
§ 371 (c)(1),
(2) Date: Jan. 11, 2018

(87) PCT Pub. No.: WO2017/011618
PCT Pub. Date: Jan. 19, 2017

(65) Prior Publication Data
US 2018/0200381 A1    Jul. 19, 2018

Related U.S. Application Data

(60) Provisional application No. 62/192,782, filed on Jul. 15, 2015.

(51) Int. Cl.
*C12N 15/11* (2006.01)
*A61K 47/68* (2017.01)
(Continued)

(52) U.S. Cl.
CPC ...... *A61K 47/6807* (2017.08); *A61K 31/5377* (2013.01); *A61K 45/06* (2013.01);
(Continued)

(58) Field of Classification Search
None
See application file for complete search history.

(56) References Cited

U.S. PATENT DOCUMENTS

2010/0286241 A1   11/2010   Xie et al.
2011/0229580 A1   9/2011    Srivastava et al.
(Continued)

FOREIGN PATENT DOCUMENTS

WO   2011014457 A1   2/2011
WO   2012143508 A1   10/2012
(Continued)

OTHER PUBLICATIONS

Elzoghby, Gelatin-based nanoparticles as drug and gene delivery systems: Reviewing three decades of research, 2013, Journal of Controlled Release, 172: 1075-1091 (Year: 2013).*

(Continued)

*Primary Examiner* — Ekaterina Poliakova-Georgantas
(74) *Attorney, Agent, or Firm* — Greer, Burns & Crain, Ltd.; Steven P. Fallon

(57) ABSTRACT

Provided are nanoparticle conjugates comprising a drug encapsulated in a gelatin nanoparticle the surface of which is functionalized with an antibody to which a siRNA is linked. Methods with the nanoconjugates for treating diseases are provided as well.

10 Claims, 24 Drawing Sheets

Specification includes a Sequence Listing.

(51) Int. Cl.
- *A61K 45/06* (2006.01)
- *A61K 47/69* (2017.01)
- *A61P 35/00* (2006.01)
- *A61K 31/5377* (2006.01)
- *A61K 47/54* (2017.01)

(52) U.S. Cl.
CPC ........ *A61K 47/549* (2017.08); *A61K 47/6849* (2017.08); *A61K 47/6851* (2017.08); *A61K 47/6931* (2017.08); *A61P 35/00* (2018.01)

(56) References Cited

U.S. PATENT DOCUMENTS

| | | | |
|---|---|---|---|
| 2013/0195752 A1* | 8/2013 | Panyam | A61K 47/42 424/1.11 |
| 2014/0105828 A1 | 4/2014 | Yang | |

FOREIGN PATENT DOCUMENTS

| | | | |
|---|---|---|---|
| WO | 2013078271 A1 | 5/2013 | |
| WO | 2014002108 A1 | 1/2014 | |

OTHER PUBLICATIONS

Aksamitiene et al., "Cross-talk between mitogenic Ras/MAPK and survival PI3K/Akt pathways: a Fine balance", Biochemical Society Transactions, vol. 40, part 1, pp. 139-146, 2012.

Aleman et al., "Comparison of siRNA-induced off-target RNA and protein effects", RNA, vol. 13, pp. 385-395, 2007.

Baker and Der, "Cancer: Drug for an undruggable protein", Nature, vol. 497, pp. 577-578, May 30, 2013.

Balthasar et al., "Preparation and characterisation of antibody modified gelatin nanoparticles as drug carrier system for uptake in lymphocytes", Biomaterials, vol. 26, pp. 2723-2732, Sep. 11, 2004.

Baumer et al., "Antibody-Mediated Delivery of Anti-KRAS-siRNA In Vivo Overcomes Therapy Resistance in Colon Cancer", Clinical Cancer Research, vol. 21, pp. 1383-1394, Mar. 15, 2015.

Bermudez et al., "Post-translational regulation of the ERK phosphatase DUSP6/MKP3 by the mTOR pathway", Oncogene, vol. 27, pp. 3685-3691, 2008.

Bermudez et al., "Post-Transcriptional Regulation of the DUSP6/MKP-3 Phosphatase by MEK/ERK Signaling and Hypoxia", Journal of Cellular Physiology, vol. 226, pp. 276-284, 2010.

Brand et al., "AXL Mediates Resistance to Cetuximab Therapy", Cancer Research, vol. 74, pp. 5152-5164, Sep. 15, 2014.

Cai et al., "Gab1 and SHP-2 promote RAS/MAPK regulation of epidermal growth and differentiation", The Journal of Cell Biology, vol. 159, No. 1, pp. 103-112, Oct. 14, 2002.

Chen et al., "Cigarette Smoking Induces Overexpression of Hepatocyte Growth Factor in Type II Pneumocytes and Lung Cancer Cells", Am. J. Cell. Mol. Biol., vol. 34, pp. 264-273, Oct. 27, 2005.

Chiang, "Hepatocyte Growth Factor Induces Hypoxia-Related Interleukin-8 Expression in Lung Adenocarcinoma Cells", Molecular Carcinogenesis, vol. 48, pp. 662-670, Jan. 30, 2009.

Derfus et al., "Targeted Quantum Dot Conjugates for siRNA Delivery", Bioconjugate Chem., vol. 18, pp. 1391-1396, Jul. 14, 2007.

Derman et al., "HGF-mediated chemotaxis and tubulogenesis require activation of the phosphatidylinositol 3-kinase", American Journal of Physiology, vol. 268, F1211-F1217, 1995.

Ding et al., "Gold Nanoparticles for Nucleic Acid Delivery", Molecular Therapy, vol. 22, No. 6, pp. 1075-1083, Apr. 1, 2014.

Faivre et al., "A simple HPLC-UV method for the simultaneous quantification of gefitinib and erlotinib in human plasma", Journal of Chromatography B, vol. 879, pp. 2345-2350, Jun. 22, 2011.

Furcht et al., "Diminished functional role and altered localization of SHP2 in non-small cell lung cancer cells with EGFR-activating mutations", Oncogene, vol. 32, pp. 2346-2355, Jul. 9, 2012.

Giljohann et al., "Gene Regulation with Polyvalent siRNA-Nanoparticle Conjugates", J. Am. Chem. Soc., vol. 131, No. 6, pp. 2072-2073, Feb. 18, 2009.

Gilleron et al., "Image-based analysis of lipid nanoparticle-mediated siRNA delivery, intracellular trafficking and endosomal escape", Nature Biotechnology, vol. 31, No. 7, pp. 638-649, Jun. 23, 2013.

Giubellino et al., "Grb2 Signaling in Cell Motility and Cancer", Expert Opin. Ther. Targets., vol. 12, No. 8, pp. 1021-1033, Aug. 2008.

Gu and Neel, "The 'Gab' in signal transduction", TRENDS in Cell Biology, vol. 13, No. 3, pp. 122-130, Mar. 2003.

Hickerson et al., "Stability Study of Unmodified siRNA and Relevance to Clinical Use", Oligonucleotides, vol. 18, pp. 345-354, 2008.

Hoeben et al., "Role of Grb2-Associated Binder 1 (Gab1) in Epidermal Growth Factor Receptor (EGFR)-Induced Signaling in Head and Neck Squamous Cell Carcinoma", Int. J. Cancer., vol. 132, No. 5, pp. 1042-1050, Mar. 1, 2013.

Jeannot et al., "The PI3K/AKT pathway promotes gefitinib resistance in mutant KRAS lung adenocarcinoma by a deacetylase-dependent mechanism", International Journal of Cancer, vol. 134, pp. 2560-2571, 2014.

Jemal et al., "Cancer Statistics, 2010", CA Cancer J. Clin., vol. 60, No. 5, pp. 277-300, Sep./Oct. 2010.

Lazzara et al., "Impaired SHP2-Mediated Extracellular Signal-Regulated Kinase Activation Contributes to Gefitinib Sensitivity of Lung Cancer Cells with Epidermal Growth Factor Receptor-Activating Mutations", Cancer Research, vol. 70, pp. 3843-3850, 2010.

Liu et al., "BAG3 gene silencing sensitizes leukemic cells to Bortezomib-induced apoptosis", FEBS Letters, vol. 583, pp. 401-406, Dec. 25, 2008.

Liu et al., "Survivin gene silencing sensitizes prostate cancer cells to selenium growth inhibition", BMC Cancer, vol. 10, No. 418, 2010.

Mao et al., "KRAS mutations and resistance to EGFR-TKIs treatment in patients with non-small cell lung cancer: A meta-analysis of 22 studies", Lung Cancer, vol. 69, pp. 272-278, 2010.

Ming et al., "Bioconjugates for Targeted Delivery of Therapeutic Oligonucleotides", Advanced Drug Delivery Reviews, vol. 87, pp. 81-89, Feb. 14, 2015.

Ochi et al., "SRC mediates ERK reactivation in gefitinib resistance in non-small cell lung cancer", Experimental Cell Research, vol. 322, pp. 168-177, Jan. 15, 2014.

Oh and Park, "siRNA delivery systems for cancer treatment", Advanced Drug Delivery News, vol. 61, pp. 850-862—May 5, 2009.

Ostrem et al., "K-RAS (G12C) inhibitors allosterically control GTP affinity and effector interactions", Nature, vol. 503 (7477), pp. 548-551, Nov. 28, 2013.

Saraswathy and Gong, "Recent developments in the co-delivery of siRNA and small molecule anticancer drugs for cancer treatment", Materials Today, vol. 17, No. 6, pp. 298-306, Jul./Aug. 2014.

Schmid et al., "EGFR/KRAS/BRAF Mutations in Primary Lung Adenocarcinomas and Corresponding Locoregional Lymph Node Metastases", Clin. Cancer Res., vol. 15, No. 14, pp. 4554-4560, Jul. 15, 2009.

Schneeberger et al., "Inhibition of SHP2 suppresses mutant EGFR-induced lung tumors in transgenic mouse model of lung adenocarcinoma", Oncotarget, vol. 6, No. 8, pp. 6191-6202, Jan. 31, 2015.

Srikar et al., "Targeted nanoconjugate codelivering siRNA and tyrosine kinase inhibitor to KRAS mutant NSCLC dissociates GAB1-SHP2 post oncogene knockdown", Scientific Reports, vol. 6, pp. 1-14, Aug. 17, 2016.

Sunaga et al., "Knockdown of Oncogenic KRAS in Non-Small Cell Lung Cancers Suppresses Tumor Growth and Sensitizes Tumor Cells to Targeted Therapy", Molecular Cancer Therapeutics, vol. 10, No. 2, pp. 336-346, Feb. 2011.

Whitehead et al., "Knocking down barriers: advances on siRNA delivery", Nature Reviews Drug Discovery, vol. 8, pp. 129-138, Feb. 2009.

(56) References Cited

OTHER PUBLICATIONS

Xu and Wang, "Delivery systems for siRNA drug development in cancer therapy", Asian Journal of Pharmaceutical Sciences, vol. 10, pp. 1-12, Aug. 28, 2004.

Yu et al., "ERK Negatively Regulates the Epidermal Growth Factor-mediated Interaction of Gab1 and the Phosphatidylinositol 3-Kinase", The Journal of Biological Chemistry, vol. 277, No. 22, Issue of May 31, 2002, pp. 19382-19388.

Yuan and Cantley, "PI3K pathway alterations in cancer: variations on a theme", Oncogene, vol. 27, pp. 5497-5510, 2008.

Yun et al., "The T790M mutation in EGFR kinase causes drug resistance by increasing the affinity for ATP", PNAS, vol. 105, No. 6, pp. 2070-2075, Feb. 12, 2008.

Zhang et al., "Dual specificity phosphatase 6 (DUSP6) is an ETS-regulated negative feedback mediator of oncogenic ERK signaling in lung cancer cells", Carcinogenesis, vol. 31, No. 4, pp. 577-586, 2010.

Zhang et al., "Receptor-Specific Regulation of Phosphatidylinositol 3'-Kinase Activation by the Protein Tyrosine Phosphatase Shp2", Molecular and Cellular Biology, vol. 22, No. 12, pp. 4062-4072, Jun. 2002.

Zhi et al., Potential Prognostic Biomarker CD73 Regulates Epidermal Growth Factor Receptor Expression in Human Breast Cancer, Life, vol. 64, No. 11, pp. 911-920, Nov. 2012.

Zugasti et al., "RAF-MEK-ERK Cascade in Anoikis is Controlled by Rac1 and Cdc42 via Akt", Molecular and Cellular Biology, vol. 21, No. 19, pp. 6706-6717, Oct. 2001.

Blaine R. Copenheaver, International Search Report for Application No. PCT/US2016/042191, dated Oct. 14, 2016.

\* cited by examiner

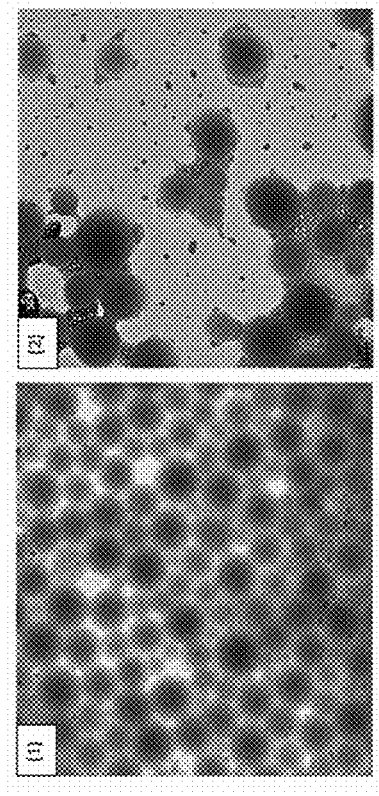
FIG. 7A
FIG. 7B
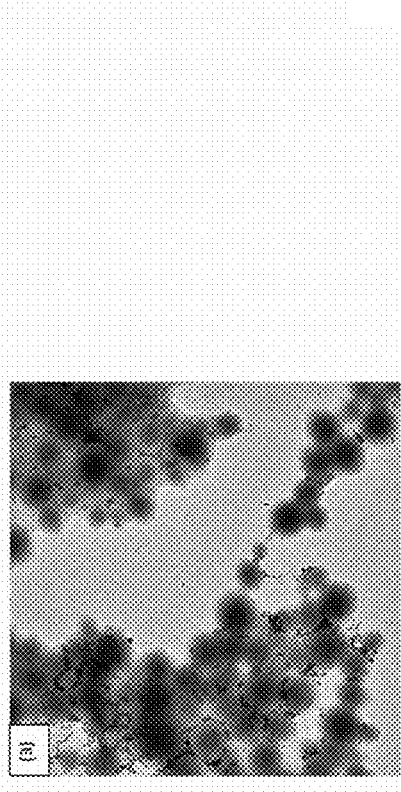
FIG. 7C

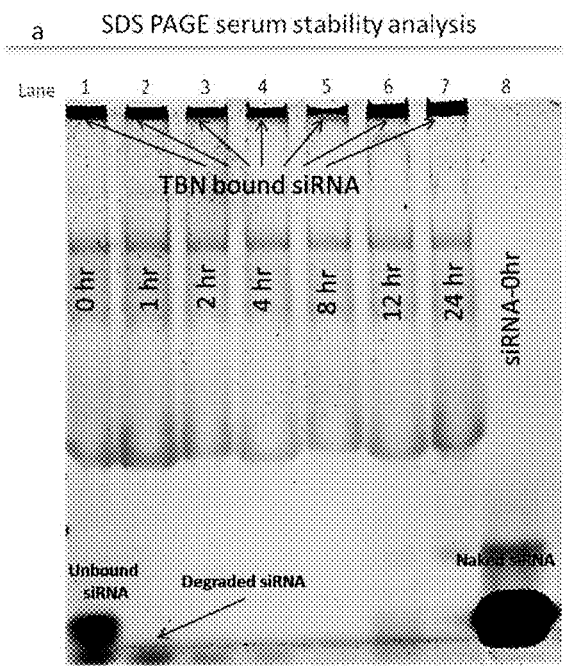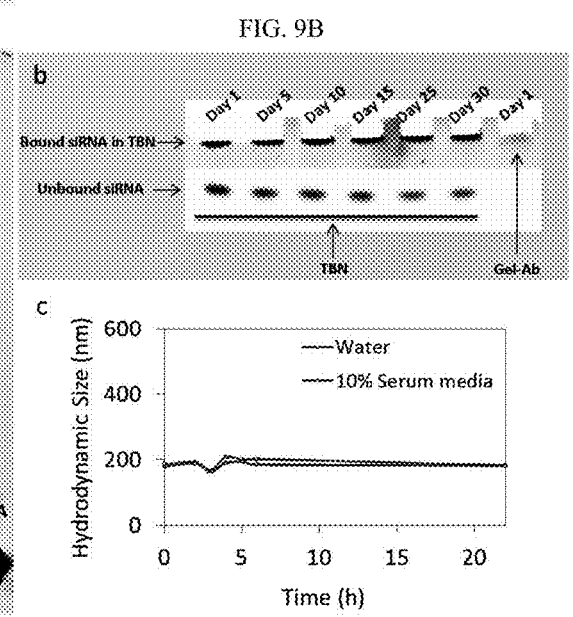
FIG. 9A  FIG. 9B  FIG. 9C

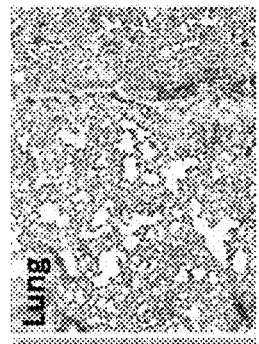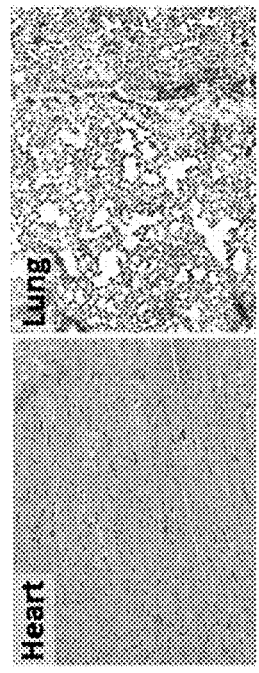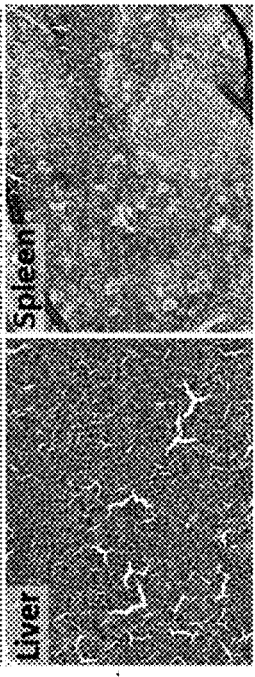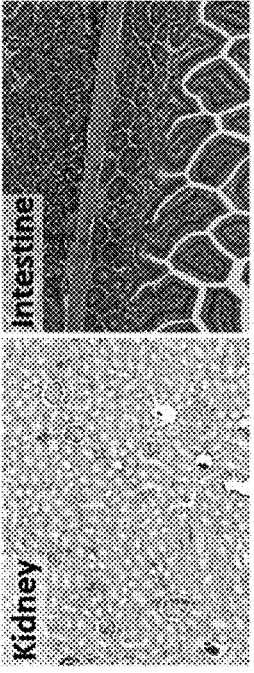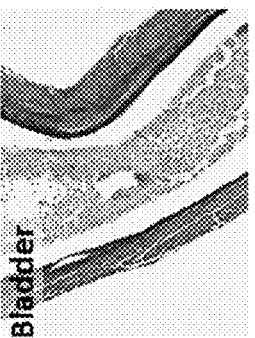
FIG. 21A FIG. 21B FIG. 21C FIG. 21D FIG. 21E FIG. 21F FIG. 21G

TARGETED NANOPARTICLE CONJUGATE AND METHOD FOR CO-DELIVERY OF SIRNA AND DRUG

CROSS-REFERENCE TO RELATED APPLICATIONS

This application claims the benefit of priority to U.S. Provisional Patent Application 62/192,782, filed Jul. 15, 2015, the entire disclosure of which is incorporated herein by reference.

TECHNICAL FIELD

A field of the invention is nanomaterials. Example applications of the invention include in vivo treatments, including therapy of human cancer.

BACKGROUND

Stable and targeted delivery of small interfering RNA (siRNA) to diseased sites has been a key obstacle for clinical translation of siRNA based therapeutics. Transport of siRNA to cytoplasm for effecting gene therapy is another obstacle. Antibodies that bind to specific biomarkers in the cell and also aide in retaining the stability of siRNA provide a partial solution for stable delivery, however they fail to deliver siRNA effectively to cytoplasm of the infected cells.

Small interfering RNA (siRNA) is a promising therapeutic route for several infected cell diseases. In the case of cancer, it is known that standalone siRNA does not cause cytotoxicity to cells to the extent that infected cells are completely eliminated. A knockdown of an oncogene merely silences the gene of interest, and consequently facilitates the affected cancer cells to adapt and adopt a different pathway of survival. For definitive cytotoxic action, a molecule complementing the siRNA for inducing inclusive toxicity needs to be delivered simultaneously and at appropriate proportions to the infected cells where the siRNA is delivered. Conversion of an un-druggable ailment to a drug responsive one through simultaneous delivery of siRNA and cytotoxin to infected cells will pave way for using siRNA therapy for drug-resistant diseases. Indeed, the efficacy would be higher when this complementarily paired system is targeted towards specific biomarkers present on the surface of the infected cells.

In accordance to numerous publications on the delivery of siRNA, the essential parameters that govern effective delivery of siRNA can be categorized into (1) stability of siRNA, (2) targeting the siRNA, (3) effective gene silencing, and (4) cytotoxicity and off-target effects. For stable siRNA delivery, Mirkin and co-workers reported AuNP functionalized with oligoethylene glycol-siRNA. The study showed that the OEG performed two essential functions in combination with gold nanoparticles; namely, polyvalency for inducing proton sponge effect, and relatively higher stability of siRNA in serum. The conjugate showed specific and higher knockdown of luciferase in HeLa cells compared to transfection with lipofectamine. Subsequent induction of cytotoxins and cellular response was not a part of the study. For targeting siRNA to specific biomarkers, Cuellar et al. studied siRNA-antibody conjugates (using THIOMAB) with various sets of antibodies and cell lines for targeted gene silencing.

The authors reported that, although the conjugates were very well defined with high targeting potential, the gene silencing aspect was not very effective for several cases. The reason for ineffective gene silencing was due to a relatively low proton-sponge effect for endosomal escape of siRNA. Again, subsequent cytotoxicity related studies were not a part of the work.

Non-Small Cell Lung Cancer (NSCLC) NSCLC is diagnosed in an estimated 220,000 patients each year with five-year overall survival rates of 16 percent.

A recent report confirmed that 16 percent of NSCLC patients carry oncogenic KRAS mutation. A potent drug targeted against KRAS mutation has not yet been developed and the objective response rate with the current standard of care is just three percent. An earlier report had suggested siRNA therapy renders the undruggable KRAS mutant cells to become susceptible to Tyrosine Kinase Inhibitors (TKI). Short interfering RNA (siRNA) is a well-known approach for effecting gene therapy to provide subsequent sensitization towards complementary therapeutic agents. However, stable delivery of siRNA is a significant challenge due to its high degradation rate in the presence of serum proteins and enzymes.

To overcome this challenge, several nanoparticle-based carrier systems have been attempted and those include retroviral vectors, liposomes, polymeric, and metallic nanoparticles. In these reported studies the physicochemical and surface properties of the particle were modified for delivering the siRNA to cytoplasm of the infected cells. Unfortunately, these nanoparticles suffer from serious limitations such as stability issues during synthesis, premature release in serum, inefficient endosomal escape, and interferon response. Importantly, oncogene knockdown alone has less impact on the cancer cell apoptosis since the cells tend to adopt another effector pathway for survival. Therefore, a need for complementary drug for initiating the apoptosis post knockdown is needed. Indeed, drugging cells separately and exogenously post oncogene knockdown has been reported earlier. A combined delivery system wherein, co-delivery of a drug along with siRNA to impede growth and survival of the cell has also been attempted. The relevance of the combined delivery is to ensure the complementary drug enters the same cells that are affected by siRNA at a predetermined appropriate proportion and time for causing cellular apoptosis. However, incorporation of siRNA (with minimal degradation) with a drug and a biomarker-targeting antibody into a single platform is synthetically challenging. Thus, stable and targeted delivery with concomitant cytotoxic action to cancer cells continues to be at early exploratory stages.

Significant efforts have been made to understand the downstream effect of oncogene knockdown mediated via siRNA. Cancer cells have several parallel working pathways, with one primary effector pathway coupled to several parallel effector pathways. The parallel pathways remain dormant until the working pathway is disrupted. Change in the protein expression levels upon knock down of oncogene present in the primary pathway results in change of downstream protein and gene expression levels regulated by complex cellular mechanism.

This mode of intra-cellular functioning adaptation evolves to drug resistance within cancer cells that are previously responding to therapy. On the other hand, KRAS mutant adenocarcinoma of NSCLC remains undruggable. While mutations occur at variation position of KRAS, oncogenic effect at codon 12 (Glycine-12 to Cysteine, G12C) of KRAS is the most commonly occurring mutation and yet to receive a dedicated drug. Although, in recent times, few attempts have been made for targeting G12C mutation through a small molecule inhibitor, RNAi therapy is emerging as a promising tool that could be applied across all types of mutations supplemented with currently approved drugs.

The present inventors have determined that depending on siRNA delivery through physical mixtures, electrostatic interaction of carrier vehicle and siRNA is not very effective. The low effectiveness can be attributed to the lack of definitive structural properties, and also possibly due to agglomeration of particles.

To date, no drug has been discovered which can inhibit the mutant KRAS for effecting therapy. Also, kinetics involved in the RAS pathway is highly complex and interlinked with several other intracellular pathways to assist in cell proliferation. Effect of cytotoxicity induction post oncogene knockdown was reported by Sunaga et al. for KRAS mutant NSCLC. In their report, un-druggable lung adenocarcinoma with K-Ras mutation showed sensitivity to a tyrosine kinase inhibitor (gefitinib) after knocking down K-Ras oncogene with retroviral vector carrying siRNA. The report is also one of the few wherein it was determined that post-knockdown, the NSCLC cells adopted an alternate downstream pathway for survival. The downstream Ras pathway upon knockdown of KRAS mutant gene decreased the protein level expression of the Ras pathway downstream protein pMEK, and also affected pAKT. The protein down-regulation effected an increase in pEGFR which is absent in the otherwise untreated cells, suggesting an alternate route of cellular mechanism. However, two main challenges limit the translation of retroviral vector strategy for the delivery of siRNA. Firstly, a retroviral vector carrying siRNA and functionalized with a targeting agent such as an antibody for targeting specific biomarkers is a synthetic challenge and has not been reported to this date to our knowledge. Secondly, ensuring the cytotoxin (such as for example, gefitinib) internalizes within all the cells altered by siRNA at appropriate relative proportions is difficult. An off-target interferon response due to retroviral vector might also create an issue for clinical translation.

Another cancer treatment target is AXL receptor which is overexpressed in various types of cancers. The AXL overexpression by some cancer cells has been reported in literature as a cause of cancer cells resistance to EGFR-targeting therapy. AXL (TAM receptor tyrosine kinase family; 140 kDa) is linked to cancer proliferation, migration and cause the subsequent resistance to small molecule tyrosine kinase inhibitors. AXL is also known to affect the PI3/Akt signaling pathways and induce a mutation in EGFR as a tyrosine kinase switch.

SUMMARY OF THE INVENTION

Provided is a nanoparticle conjugate comprising a small interfering RNA (siRNA) linked to an antibody that is bonded to the surface of a gelatin nanoparticle that physically encapsulates a drug. This conjugate delivers the drug and siRNA simultaneously and selectively to a targeted cell, such as a cancer cell. In the conjugate, one end of siRNA may be coupled to an epidermal growth factor receptor (EGFR) targeting monoclonal antibody via a thio-ether bond, and a lysine functional group present on the antibody is bridged with carboxyl groups present on the gelatin nanoparticle. The drug may comprise a tyrosine kinase inhibitor drug. Some conjugates comprise cisplatin, oxaliplatin, gefitinib or erlotinib. In the conjugate, the siRNA may be a siRNA specific to mutant KRAS or siRNA specific to AXL. Some conjugates comprise siRNA comprising 5'-GUUGGAGCUUGUGGCGUAGUUUU-3' (SEQ ID NO. 1) annealed with 5'-AACUACGCCACAAGCUCCAACUU-3' (SEQ ID NO. 2). Some conjugates comprise siRNA comprising 5'-GGAACUGCAUGCUGAAUGAUU-3' (SEQ ID NO. 3) annealed with 5'-UCAUUCAGCAUGCAGUUCCUU-3' (SEQ ID NO. 4).

Methods of forming the nanoparticle conjugate are provided as well, and comprise encapsulating the drug in the gelatin nanoparticle, bonding the antibody to the surface of the gelatin nanoparticle, and linking the siRNA to the antibody via a thio-ether bond.

Methods of disease treatment are also provided and comprise adminstering to a patient a nanoconjugate comprising a small interfering RNA (siRNA) linked to an antibody bonded to the surface of a gelatin nanoparticle which encapsulates a drug. The nanoconjugates can be used for treating cancer, including metastatic cancer. Various cancers can be treated, including non-small lung carcinoma, brain tumor, colon cancer, head and neck cancer, prostate cancer, breast cancer or stomach cancer. In some methods of treatment, a patient is administered the nanoconjugate in which the drug is gefitinib, the antibody is EGFR-targeting antibody CETUXIMAB™ and the siRNA comprises the oligonucleotide with SEQ ID NO. 1 annealed with the oligonucleotide with SEQ ID NO. 2. These patients can be tested for KRAS mutations prior to the administration of the nanoconjugate.

BRIEF DESCRIPTION OF THE DRAWINGS

FIGS. 7A-7C are TEM images of gelatin nanoparticles (FIG. 7A), antibody functionalized gelatin nanoparticles (FIG. 7B) and nRAGeD (FIG. 7C).

FIGS. 9A-9C are stability assays for nRAGeD. FIG. 9A is a SDS-PAGE of the time related serum stability analysis. FIG. 9B is a 30-day storage stability analysis of nRAGeD stored at −50° C. FIG. 9C is an in vitro stability study of nRAGeD as analyzed by a hydrodynamic size in biological media.

FIG. 21 is a photomicrograph of H&E stained sections of mouse organs (n=5) treated with nRAGeD.

FIG. 24A shows the pathway in cancer cells with mutated RAS. FIG. 24B shows the disruption of the RAS signaling pathway by siRNA. FIG. 24C shows the further impediment of the cancer cells by gefitinib.

DETAILED DESCRIPTION

Figure 1:
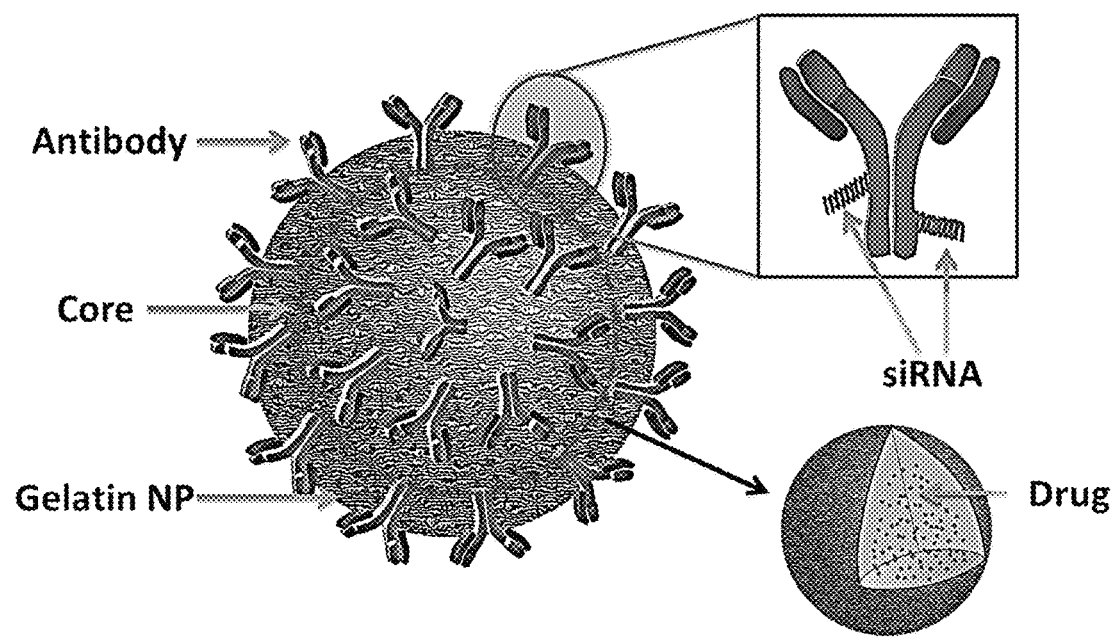
FIG. 1 is a schematic diagram of nRAGeD comprising a gelatin nanoparticle as a carrier. The surface of the gelatin nanoparticle is functionalized with an antibody. siRNA is covalently attached to the antibody via the thio-ether link. The core of the gelatin nanoparticle contains a drug.

Provided is a nanoparticle conjugate which is referred to as nRAGeD (abbreviated from "RNA-Antibody-Gelatin-Drug Nanoconjugate") and which comprises a small interfering RNA (siRNA) linked to an antibody that is bonded to the surface of a gelatin nanoparticle that physically encapsulates a drug. As shown in FIG. 1, the nRAGeD, generally 10, comprises a gelatin nanoparticle (1) which encapsulates a drug (2) in the core (3) of the gelatin nanoparticle (1). An antibody (4) is bonded to the surface of the gelatin particle (1). The antibody (4) is covalently linked to a siRNA (5) by the thio-ether bond. The nRAGeD nanoconjugate can be used as a drug for treating various diseases, including cancer, and in particular a metastatic cancer. The nRAGeD can be also used in other treatment applications where it is desirable to deliver a drug selectively to a particular set of cells.

Various antibodies are contemplated, including an antibody that selectively recognizes and binds a receptor and/or cell surface marker displayed at the cell surface. The antibody can be an antibody or an antibody fragment which selectively recognizes and binds with high affinity and specificity to a receptor and/or cell surface marker expressed at the surface of a cancer cell. Suitable antibodies include monoclonal and polyclonal antibodies. A humanized monoclonal antibody or its functional fragment is particularly preferred. One suitable antibody includes an antibody specific to human Epithelial Growth Factor Receptor (EGFR). One particularly preferred antibody is EGFR specific chimeric (mouse/human) monoclonal antibody available under the tradename CETUXIMAB™ from Merck.

Various drugs are contemplated, including anticancer drugs such as platinum-based drugs, including cisplatin and oxaliplatin. Two drugs that are particularly preferred are gefitinib (ZD1839, N-(3-chloro-4-fluoro-phenyl)-7-methoxy-6-(3-morpholin-4-ylpropoxy)quinazolin-4-amine) and erlotinib hydrochloride (N-(3-ethynylphenyl)-6,7-bis(2-methoxyethoxy) quinazolin-4-amine).

Various siRNAs are suitable, including siRNA specific to a gene whose expression is upregulated in cancer cells. Suitable siRNA are double-stranded RNA molecules, 20-25 base pairs in length with a sequence complementary to a gene whose transcription needs to be silenced. Suitable siRNAs include those that selectively interfere with expression of genes mutated and/or overexpressed in cancer cells.

Particularly preferred are siRNAs specific to mutant KRAS, including human KRAS with a point mutation in codon 12. A particularly preferred KRAS siRNA is specific to KRAS with a point mutation G12C. These siRNAs include the KRAS G12C siRNA obtained by annealing together sense oligonucleotide comprising, consisting essentially of or consisting of 5'-GUUGGAGCUUGUG-GCGUAGUUUU-3' (SEQ ID NO. 1) with an antisense oligonucleotide comprising, consisting essentially of or consisting of 5'-AACUACGCCACAAGCUCCAACUU-3' (SEQ ID NO. 2). The 5' guanine in the oligonucleotide with SEQ ID NO. 1 can be modified with a disulfide (S—S) moiety.

Another preferred siRNA is a siRNA specific for AXL. These siRNAs include the AXL siRNA obtained by annealing together sense oligonucleotide comprising, consisting essentially of or consisting of 5'-GGAACUG-CAUGCUGAAUGAUU (SEQ ID NO. 3) with an antisense oligonucleotide comprising, consisting essentially of or consisting of 5'-UCAUUCAGCAUGCAGUUCCUU-3' (SEQ ID NO. 4). The 5' guanine in the oligonucleotide with SEQ ID NO. 3 can be modified with a disulfide (S—S) moiety.

Various gelatin types are suitable for obtaining the nanoparticle. A person of skill will understand that gelatin is a mixture of peptides and proteins produced by partial hydrolysis of collagen from different sources, such as for example pork skin and fish. The strength of gelatin is measured in "bloom." Preferably, gelatin of 200 to 300 bloom is suitable for making the nRAGeD nanoconjugate. Gelatin 300 bloom is particularly preferred.

Various technical advantages are provided by the present nRAGeD nanoconjugate. It is suitable for delivery of drugs to a particular population of cells without affecting other cells. This may be useful for delivering drugs that may be otherwise toxic or are unstable. For example, many cancer drugs which are highly efficient in eliminating cancer cells are also toxic to a patient. However, delivering such a drug tackled away in the core of the nRAGeD nanoconjugate specifically to cancer cells avoids or minimizes the damage to other non-cancer cells in a patient. Another technical advantage is the nRAGeD provides a highly efficient delivery for siRNA which otherwise degrade easily in the blood stream before reaching cells targeted for treatment.

The nRAGeD nanoconjugate provides a vehicle in which siRNA is protected from degradation. In addition, the nRAGeD is a platform which delivers several drugs simultaneously to a cell targeted for treatment. This provides a particular advantage in cancer treatment where certain cancer cells, such as for example, cancer cells with mutated KRAS, are known to switch on an alternative survival pathway in response to a first anti-cancer drug that would otherwise sentence the cancer cell to apoptosis. Thus, a patient has to be treated with a second drug.

The nRAGeD nanoconjugate is useful for treating various cancer diseases, including non-small lung carcinoma, colon cancer, head and neck cancer, prostate cancer and breast cancer.

Figures 2A, 2B, 2C:
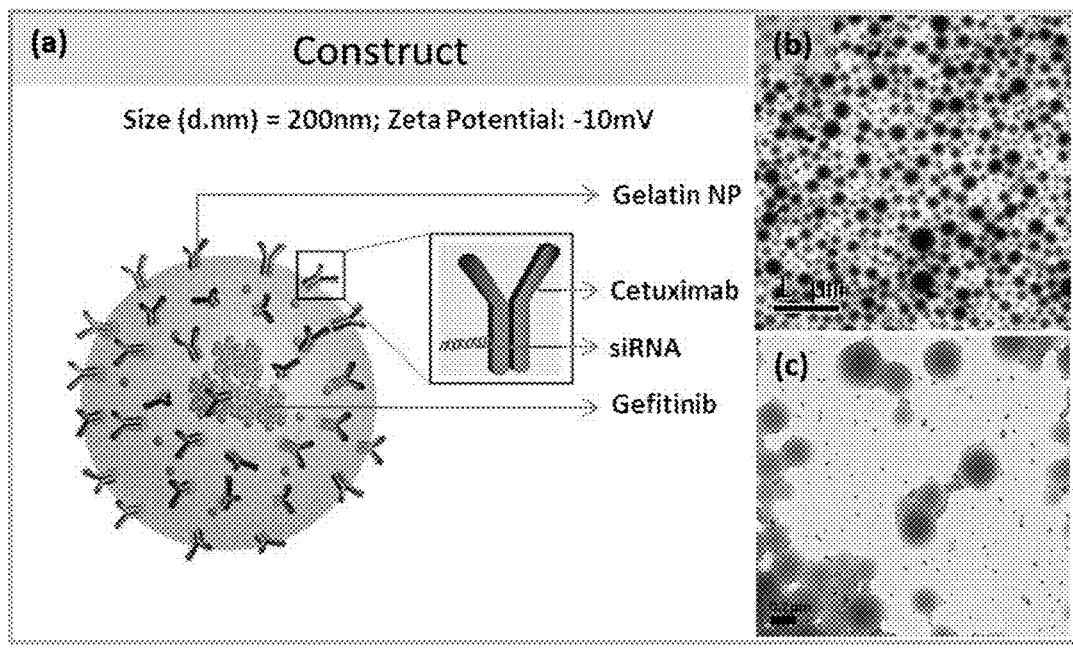
FIG. 2A is a schematic representation of the TBN nanoconjugate consisting of a gelatin nanoparticle encapsulating gefitinib and surface functionalized with CETUXIMAB™ conjugated with siRNA.
FIG. 2B is a TEM image of gelatin nanoparticles.
FIG. 2C is a TEM image of the TBN nanoconjugates.

The suitable nRAGeD nanoconjugates include a gelatin nanoparticle (GelNP) encapsulating gefitinib ($Gel_{GEF}$NP). The surface of the $Gel_{GEF}$NP nanoconjugate is functionalized with EGFR targeting antibody CETUXIMAB™ which is conjugated to KRAS G12C specific siRNA such as for example, a duplex between the oligonucleotide with SEQ ID NO. 1 and the oligonucleotide with SEQ ID NO. 2, as shown in FIG. 2A and referred to as the TBN nanoconjugate in FIG. 2A. An electronic microscope micrograph of the TBN nanoconjugate is shown in FIG. 2C, while an electronic microscope micrograph of gelatin nanoparticles is shown in FIG. 2B. The TBN nanoconjugate is useful for treating various cancer diseases, including non-small lung carcinoma, colon cancer, head and neck cancer, prostate cancer and breast cancer.

Preferred embodiments also provide in vivo treatment methods. The methods include administering a nanoparticle conjugate, also referred to as a nanoconjugate, of the invention for treatment of a disease to a patient. The treatment can be a cancer treatment. Various cancers can be treated with nRAGeD nanoconjugates, including non-small lung carcinoma, brain tumors, colon cancer, head and neck cancer, prostate cancer, breast cancer and stomach cancer.

Preferred nanoparticle conjugates of the invention provide for stable and targeted delivery of siRNA to diseased sites and also provide for transport of siRNA to the cell cytoplasm for effective gene therapy. In preferred embodiments nanoparticle conjugates, the siRNA is protected by antibodies on one side and a protein or polymeric nanoparticle on the other side that is capable of carrying its own payload within the core and deliver the ingredients to the cytoplasm of cells.

Preferred embodiments use gelatin nanoparticles that include an encapsulated drug, gefitinib. To carry siRNA, one end of siRNA is coupled to CETUXIMAB™, an epidermal growth factor receptor (EGFR) targeting monoclonal antibody via a highly stable thio-ether bond. A lysine functional group present on the antibody is bridged with carboxyl groups present on the gelatin nanoparticles. The antibody and gelatin nanoparticles act as two protective layers of a sandwich, between which resides the siRNA. In addition, a tyrosine kinase inhibitor drug, gefitinib, is encapsulated within the core of each gelatin nanoparticle. The resulting nanocomplex delivers siRNA and drug at predetermined relative proportions for effective gene knockdown and concomitant cytotoxicity.

The utility of siRNA-antibody-gelatin-gefitinib nanoparticle platform concerns converting undruggable KRAS mutant cells to gefitinib sensitive cells by knocking down the KRAS oncogene. Upon the knockdown of KRAS oncogene, the cells adopt another effector pathway for survival that is responsible for sensitization towards gefitinib. Test results suggest a new modus-operandi for stable and targeted delivery of siRNA and drug for oncogene knockdown, gene therapy and drug delivery.

Preferred embodiment nanoparticle conjugates utilize a charge-reversible protein nanoparticles that comprise a physically encapsulated drug in the core and an antibody conjugated on the surface. The siRNA of interest is linked to the surface conjugated antibody via a thio-ether bond to form an antibody-siRNA conjugate.

Figure 3:
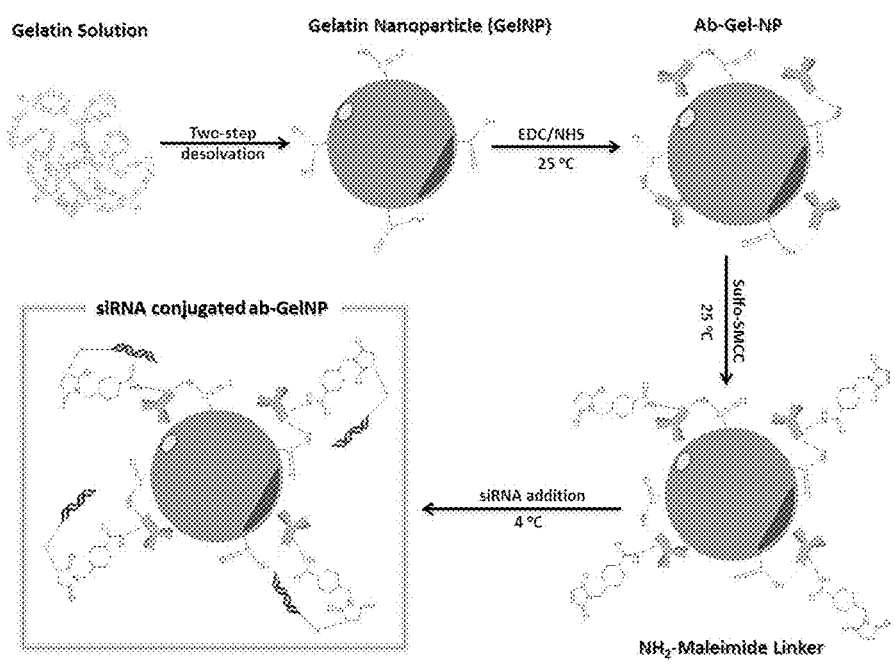
FIG. 3 is a schematic diagram of the nRAGeD synthesis.

In particular preferred embodiments, for minimal exposure of siRNA to synthetic procedures, positively charged gelatin nanoparticles (GelNP) are used as the starting material. GelNPs can be prepared via a two-step desolvation process of a gelatin solution as shown in FIG. 3. GelNPs can then be used to encapsulate a small molecule tyrosine-kinase inhibitor (TKI), gefitinib, or any other drug of choice. The resulting GelGEFNP nanoparticle can then be then used for binding antibody CETUXIMAB™ or some other antibody or an antibody fragment via a lysine functional group present on the antibody with carboxyl groups present on the surface of gelatin nanoparticles.

Other lysine residues of the antibody can be then modified with thiol-siRNAKR by using NHS-Maleimide linker molecule (sulfo-SMCC) to obtain the final construct, RNA-Antibody-Gelatin-Drug Nanoconjugate (nRAGeD). Gelatin is specifically chosen as the carrier system for enzyme-triggered release of the constituents.

Other polymers such as PLGA are good for controlled release systems. However, it is difficult to enzymatically trigger the release of the encapsulated drugs for such polymeric systems. Gelatin is prone to enzymatic degradation. This property can be exploited for delivering low doses of drugs confined within its matrix; as the drug molecules are not released until the gelatin matrix degrades. Also, positively charged gelatin nanoparticles turn negative post-surface modification with an antibody-siRNA complex, thereby providing the useful charge reversal property—an essential requirement for inducing a pH imbalance in endosomes to cause a proton-sponge effect and consequent endosomal escape of nRAGeD into the cell cytoplasm.

In this invention, it has been demonstrated that nRAGeD is a platform for targeted cell-specific delivery of a combination of siRNA and a drug for concomitant siRNA mediated oncogene knockdown and drug mediated cytotoxicity.

Preferred methods provide for the synthesis and characterization of nRAGeD to (i.) showcase its charge-reversal property, (ii.) demonstrate its ability to knock-down KRAS oncogene, and (iii.) convert un-druggable cells to drug sensitive and co-localize various constituents of the construct within the cells of interest. Also, without wishing to be bond by the theory, two probable intra-cellular delivery mechanisms of action for nRAGeD are identified and described.

As shown in FIG. 3, the synthesis of nRAGeD begins by preparing a gelatin solution. Gelatin nanoparticles (GelNP) are then produced by a two-step desolvation. Gelatin particles can be loaded with a drug (not shown in FIG. 3) during the second desolvation step.

Gelatin nanoparticles are then functionalized with an antibody Ab, resulting in Ab-Gel-NP nanoconjugate. The lysine groups of the Ab are then reacted with sulfo-SMCC to generate a reactive maleimide end to which siRNA is then conjugated with thiol-maleimide link to form a nanoconjugate carrying siRNA and also a drug if the drug was incapsulated into a gelatin nanoparticle.

Figure 4A:
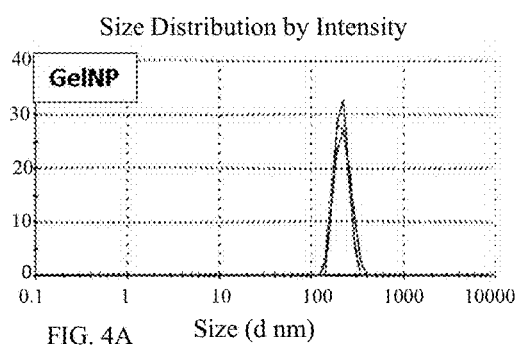
FIG. 4 is a graph reporting a hydrodynamic size of 200 (±10) nm for nRAGeD, as determined by the dynamic light scattering method using Malvern Zetasizer Nano ZS.
Figure 4B:
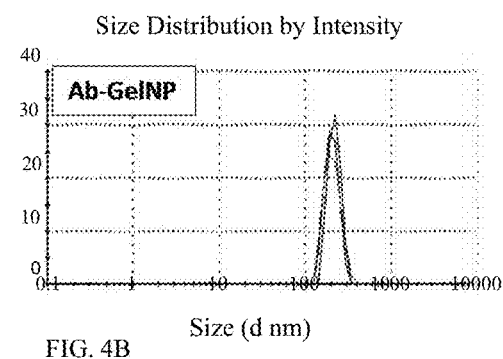
Figure 4C:
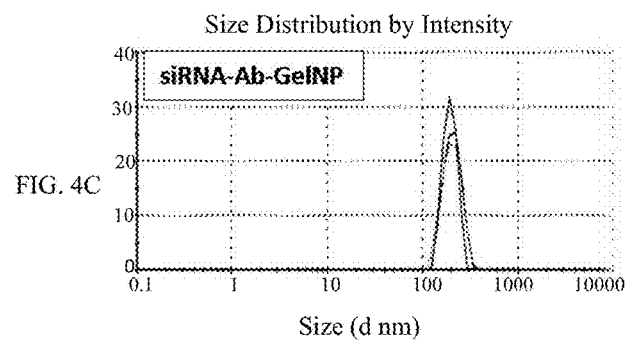

As shown in FIG. 4, nRAGeD dispersed in deionized (DI) water have an average hydrodynamic diameter of 210±10 nm with a PDI less than or equal to 0.1. The size of GelNPs with encapsulated gefitinib Gel(Gef) NPs remains the same and no significant increase in size is observed in comparison to gelatin nanoparticles not loadead with a drug.

Figure 5:
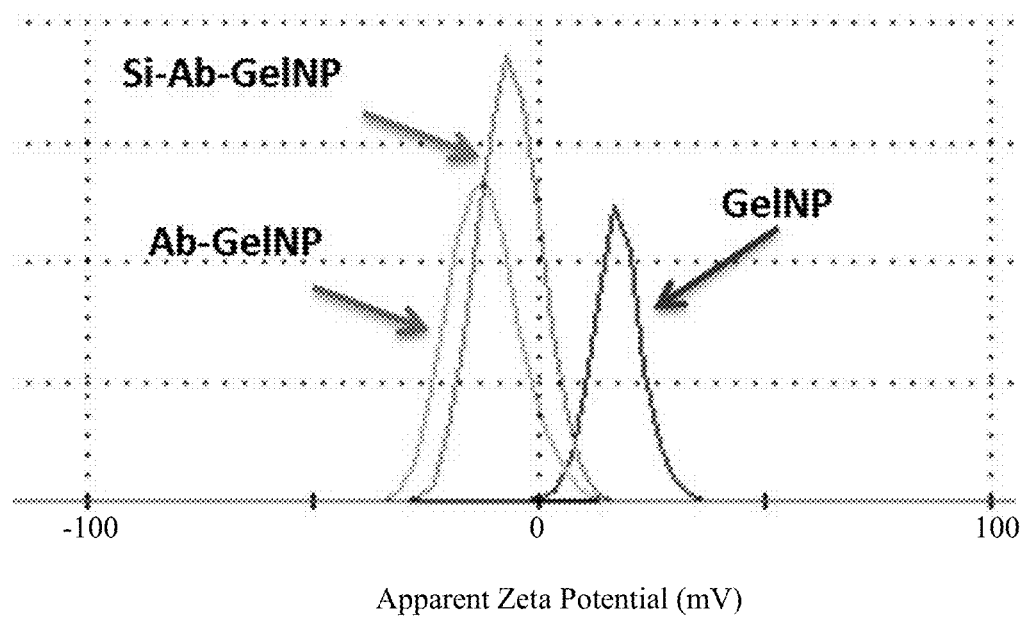
FIG. 5 reports a zeta potential for Gelatin NP (Gel NP) nanoparticles, an antibody functionalized Gelatin NP (Ab-Gel NP) nanoparticles, and nRAGeD (si-Ab-GelNP), determined by using Malvern Zetasizer Nano ZS.
Figure 6:
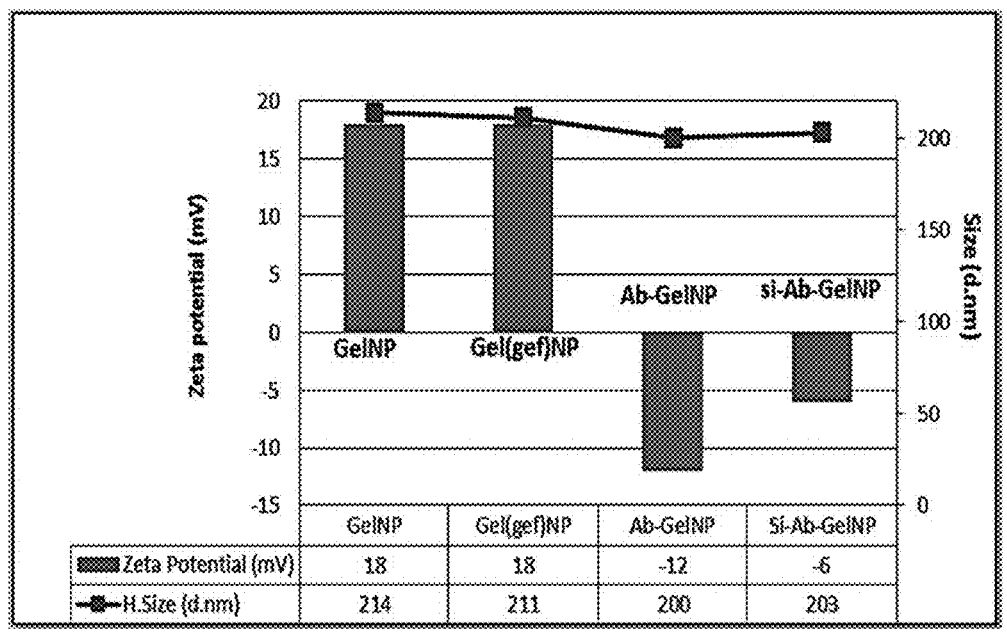
FIG. 6 reports a change in the zeta potential upon surface functionalization and siRNA addition in nRAGeD.

Zeta potential (ζ) measurements of GelNPs suspended in DI water indicate ζ of +18 mV. As shown in FIGS. 5 and 6, the ζ did not change with the encapsulated gefitinib, indicating surface properties of GelNPs remain unchanged. However, a significant change is Zeta potential was observed for nRAGeD nanoparticles which became negatively charged.

As shown in micrographs of FIGS. 7A, 7B and 7C obtained with an electronic microscope, no significant change in the size or shape of nanoparticles was observed post-surface modifications. Compare TEM images of gelatin nanoparticles (FIG. 7A), antibody functionalized gelatin nanoparticles (FIG. 7B), and nRAGeD (FIG. 7C).

A delivery of siRNA to cells of interest is a major hurdle for clinical translation. Not only is the encapsulation of siRNA within polymers or liposomes without degrading the siRNA during nanoparticle preparation is synthetically challenging, but post siRNA-NP preparation, availability of siRNA to the cells of interest for effective knockdown of concerned gene is governed by various factors which are difficult to predict or determine. A direct exposure of siRNA to the surrounding environment by mere surface functionalization of siRNA on surface of the nanoparticles without an antibody leads to its rapid degradation by serum.

The inventors have unexpectedly discovered that nRAGeD nanoconjugates overcome these challenges and protect siRNA from serum degradation without exposing siRNA to harsh chemical synthetic procedures of encapsulation. In the nRAGeD nanoconjugate, an antibody is displayed on the surface of GelNPs is used for protecting siRNA from degradation. The size and molecular weight of GelNPs (200 nm) and antibody (152 KDa) is relatively very high compared to siRNA (14 KDa). siRNA functionalized to the antibody enables a stable and covalently attached sandwich system wherein the siRNA is embedded between GelNP and and an antibody. Furthermore, siRNA incorporation to the nRAGeD nanoconjugate, being the last step of synthetic procedure can be carried out in RNAse free water without subjection to harsh chemical methods, ensures degradation-free siRNA within the nanocomplex. The premature release of siRNA can be discounted for such systems since siRNA is not physically entrapped or coated.

As shown in FIGS. 9A-9C, siRNA chemically linked to nRAGeD via an antibody remains highly stable in blood serum with only a minimal degradation after 24 hours of serum exposure (FIG. 9A). As shown in FIG. 9B, there is only a minimum degradation after 30 days of storage at −50° C. As shown in FIG. 9C, no siginicant variation in hydrodynamic size was observed after nRAGeD nanoconjugates were exposed to a biological media up to 24 hours.

Figure 11:
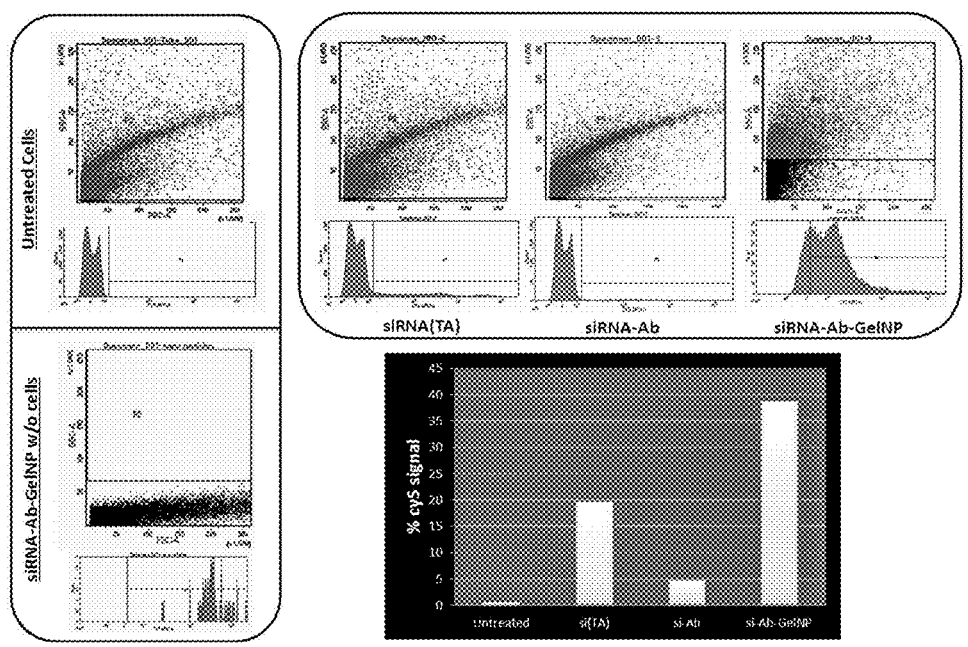
FIG. 11 is a flow cytometry analysis showing nRAGeD (siRNA-Ab-GelNP) is internalized by cancer cells almost 2 folds better as compared to transfected naked siRNA.

Another technical advantage is reported in FIG. 11 showing that the amount of siRNA internalized by cancer cells when siRNA is a part of the nRAGeD nanoconjugate is at least two fold higher than when cancer cells are transfected with naked siRNA. Thus, nRAGeD is effective as a siRNA delivery system.

As shown in FIGS. 12A, 12B, 13, 14A and 14B, nRAGeD suppresses efficently mutant KRAS and the RAS pathway in cancer cells.

Figure 16:
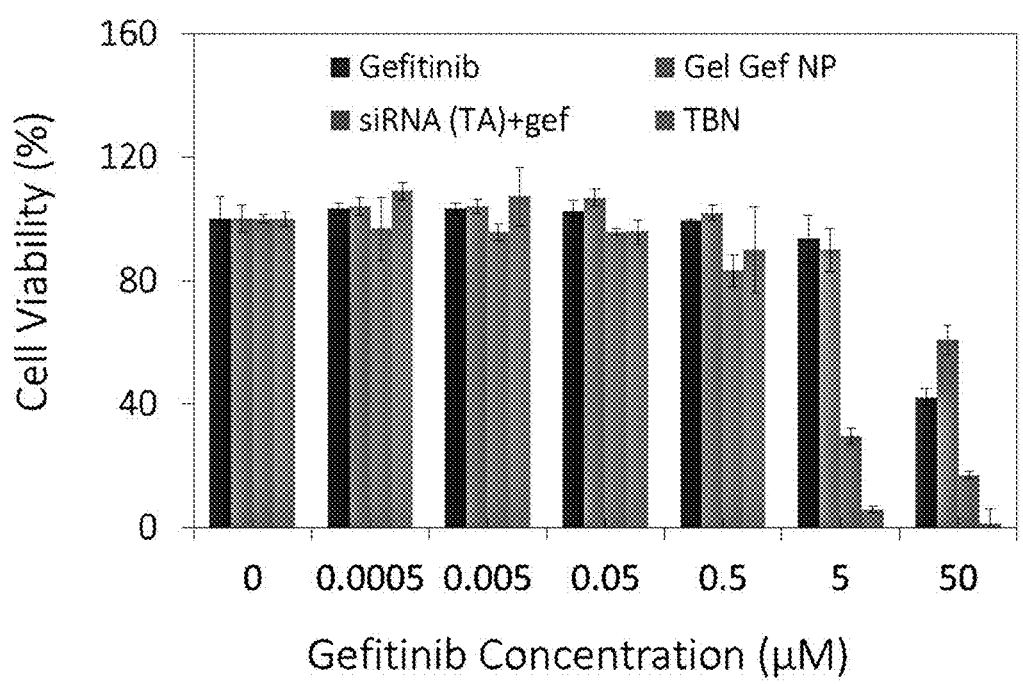
FIG. 16 is an in vitro toxicity report for lung cancer cells treated with nRAGeD.

As shown in FIG. 16, treating cancer cells with nRAGeD which delivers to the cells gefitinib together with the KRAS G12C siRNA decreases the cell viability down to 5% in comparison to treating cells with the KRAS G12C siRNA first, followed by a separate treatment with gefitinib, where the cell viability is at 25%. Thus, the combined treatment as delivered by nRAGeD has a synergistic effect.

Figure 17:
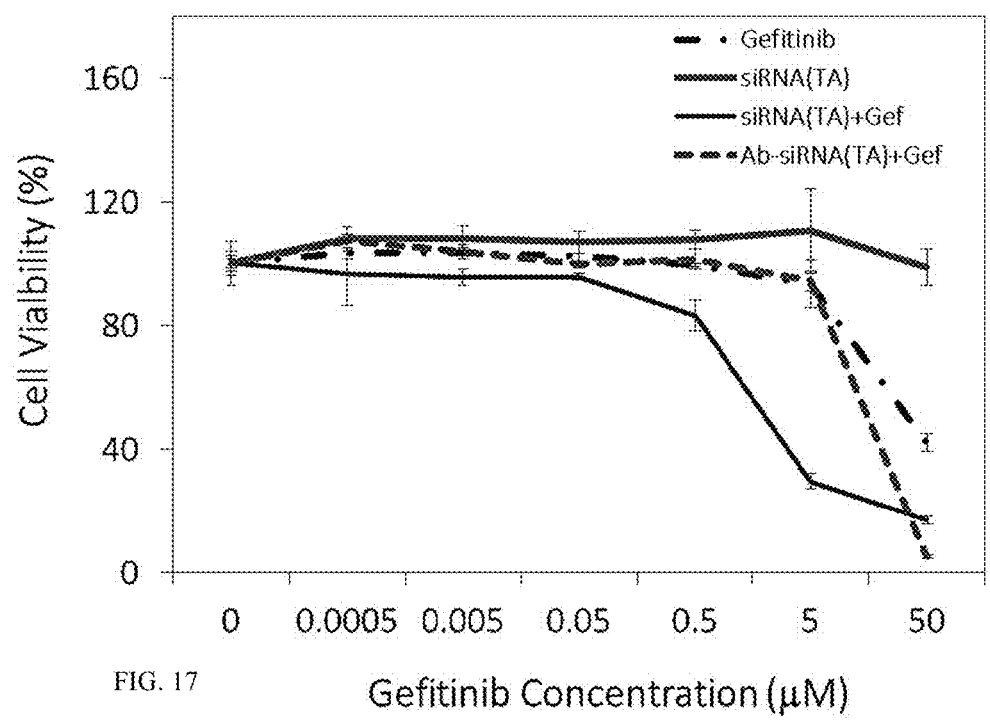
FIG. 17 is an in vitro cellular viability data after treatment with nRAGeD or control compositions.
Figure 18:
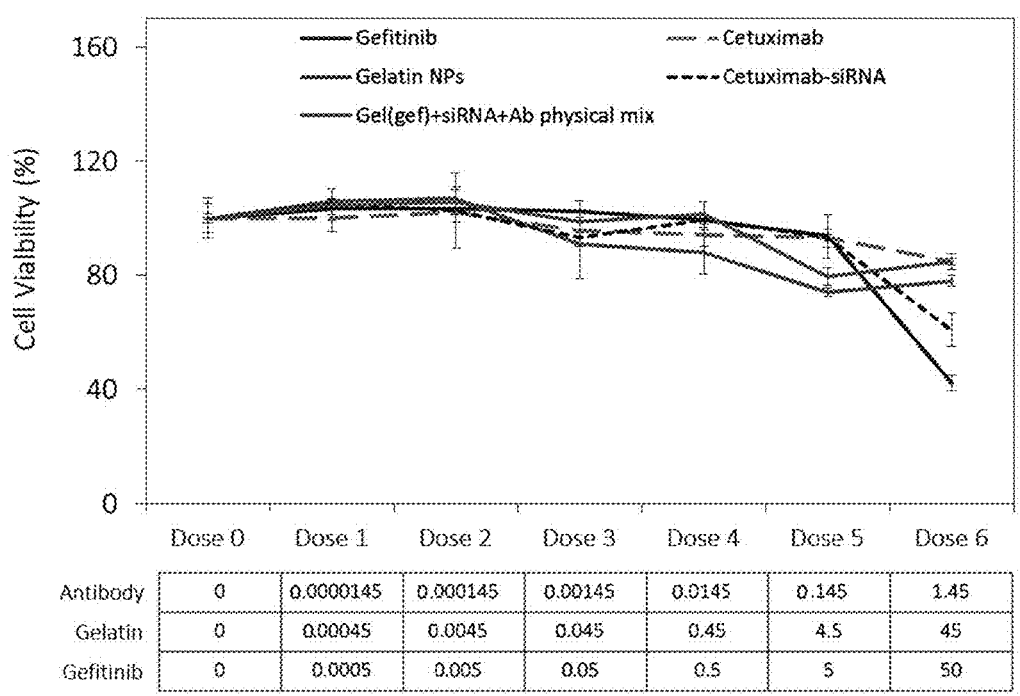
FIG. 18 reports a synergistic effect of nRAGeD on decreasing the cell viability of cancer cells.
Figure 19:
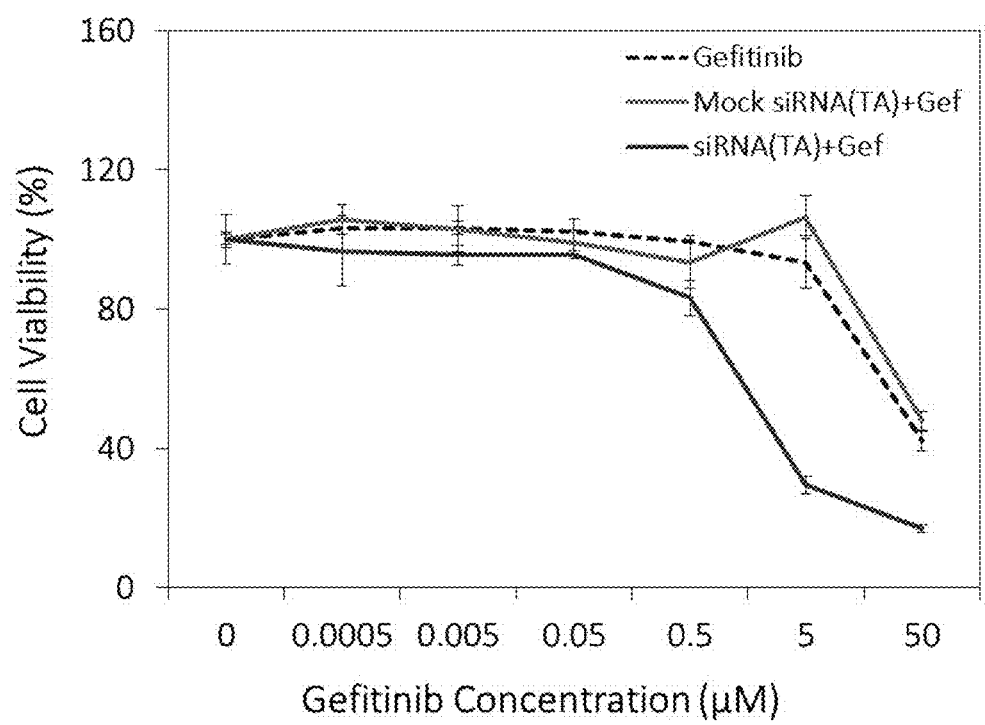
FIG. 19 reports in vitro cellular viability of cancer cells with KRAS G12C mutation transfected with mock siRNA followed by treatment with gefitinib.

The synergistic effect of nRAGeD in decreasing the viability of cancer cells is further supported by cell viability results shown in FIGS. 17, 18 and 19.

The nanoparticle conjugates of preferred embodiments with siRNA conjugated to an antibody functionalized on the surface of a gelatin nanoparticle carrying a small molecule tyrosine kinase inhibitor or some other drug protects siRNA from degradation and targets delivery of siRNA to cells which display a biomarker selected for targeting. Furthermore, the gelatin nanoparticles, used as the carrier system, enable concomitant delivery of a drug within the cells of interest and target. The platform allows loading predetermined and proportional amounts of an antibody, siRNA and drug within the carrier for effective targeting and high bioavailability to provide gene and combinational therapy.

The make up of an nRAGeD nanoparticle can be easily modified as per patient's needs wherein the siRNA, antibody and/or the encapsulated drug can be selected based on the nature and status of cancer in each individual patient.

A cancer treatment with nRAGeD may comprise an intravenous administration, where an nRAGeD nanoparticle is adminstered daily in a concentration ranging from 20 mg/kg of the patient's body weight to 250 mg/kg of the patient's body weight for a period of several days, typically from 3 to 6 days. A patient can then be monitored and tested for a decrease in cancer cells. The nRAGeD treatment can be repeated in several rounds, each of the rounds comprising several consecutive days of administration. Under some treatment plans, a patient can be treated with about 100 mg of the nRAGeD nanoconjugate per day, for a total of 5 days.

Further treatment plans may include testing a patient to identify whether the patient's cancer cells express mutated KRAS and/or AXL. Suitable tests may include sequencing, PCR, quantitative real time PCR and/or protein analysis. Based on the test results, a treatment plan may include synthesizing an si-RNA molecule specific for the type of a mutation identified in the patient, followed by preparing an nRAGeD comprising an anti-cancer small molecule drug encapsulated in a gelatin nanoparticle and functionalized with an antibody linked to the surface of the nanoparticle and linking the siRNA to the bonded antibody. The patient is then treated with the nRAGeD specifically designed for the patient's cancer cells.

Without wishing to be bound by any theory, the inventors also disclose a mechanism by which nRAGeD may affect proteins in the RAS/RAF/MEK/ERK cascade. In this inquiry, quantitative real time PCR was performed to examine dual specificity phosphatase 6 (DUSP6) and CD73 gene expression levels. DUSP6 is an important feedback loop as it exhibits antitumor profile through negative feedback regulation. An effect on the signaling cascade, therefore, must have an effect on DUSP6 levels.

Figure 22A:
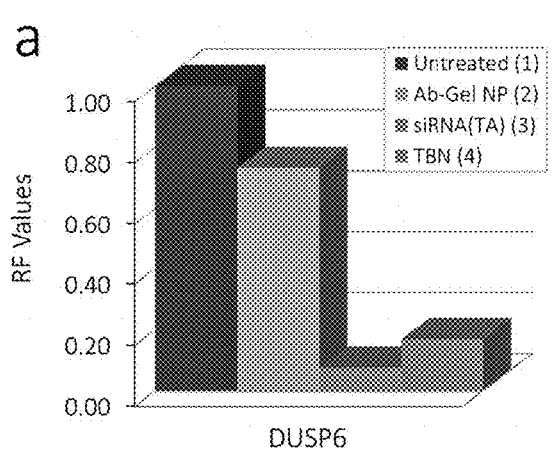
FIGS. 22A and 22B report an RT-PCR analysis for DUSP6 and NT5E in cancer cells treated with nRAGeD.

As shown in FIG. 22A, transfected siRNA and nRAGeD cells showed downregulation of DUSP6 upon knockdown. The RF values of DUSP6 post knockdown determined using real time qPCR for nanoparticle correlated well with that of transfected siRNA and was determined to be 0.17 and 0.1 for nRAGeD and siRNA respectively. In contrast, Ab-Gel-GEFNP devoid of siRNA, showed the RF value of 0.73 indicating minimal or no effect on the gene regulation. The results suggest a post-oncogene knockdown, loss of activity in the MEK/ERK cascade has a direct impact on the gene regulation of DUSP6, as shown in FIG. 22A which reports the RF values determined by quantitative real time PCR and indicates the downregulation of DUSP6 gene expression for the H23 cells treated with siRNA and nRAGeD.

Figure 22B:
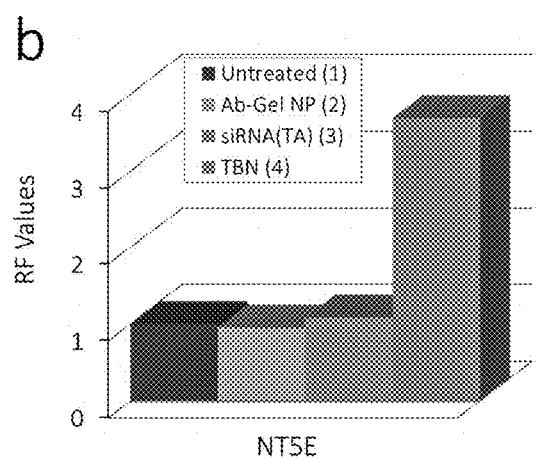

NT5E or CD73 is a predictive biomarker for overall patient's survival and progression free survival in patients harboring KRAS wild type or a KRAS mutation. As shown in FIG. 22B, the inventors observe a significant increase in the CD73 expression levels for cancer cells treated with nRAGeD and no change for cancer cells transfected with siRNA or treated with Ab-GelGEFNP devoid of siRNA. The CD73 RF value for cells treated with TBN was determined to be 3.64 compared to 1.07 and 0.95 for siRNA and Ab-GelGEFNP with no siRNA respectively, as shown in FIG. 22B which reports the RF values determined by quantitative real time PCR indicates up regulation of NT5E gene expression for the H23 cells treated with TBN. Cells treated with siRNA or CETUXIMAB™ functionalized gelatin nanoparticles showed minimal or no change in expression levels compared to the untreated cells. The increase in CD73 expression levels may be attributed to the presence of both siRNA and CETUXIMAB™ in aRAGeD.

Figure 23:
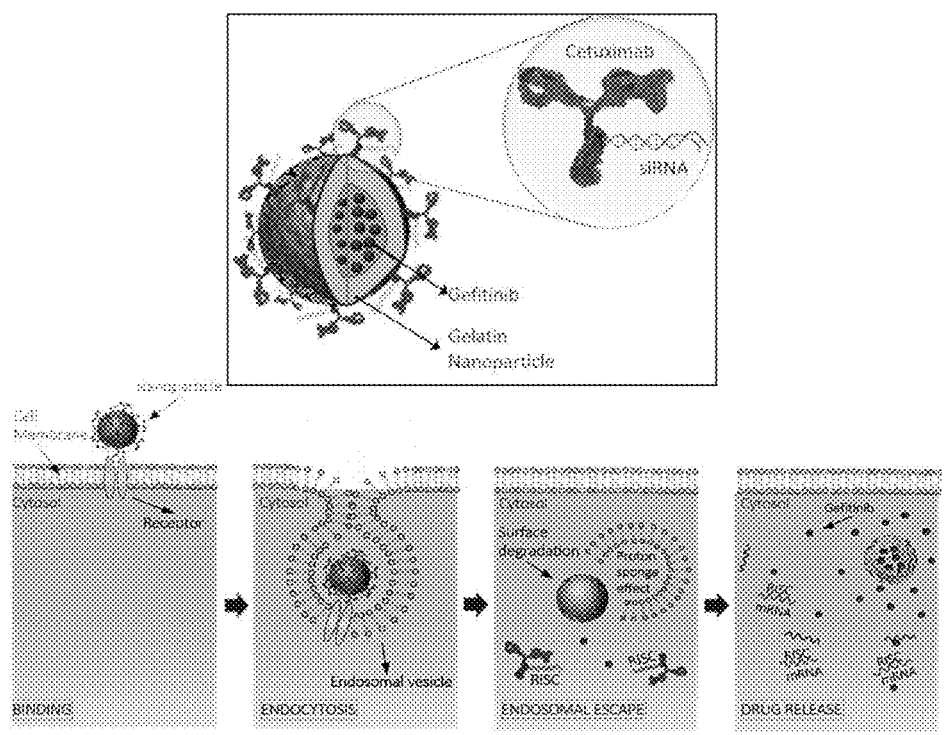
FIG. 23 is a schematic depicting the mechanism by which nRAGeD may bind to a cell surface receptor and then be internalized by the cell.

The inventors postulate that the mechanism of release of nRAGeD from endosomes to cytosol as shown in FIG. 23 and the concomitant effect on gene and protein regulation. As shown in FIG. 23, nRAGeD enters cells using a receptor mediated endocytosis and stays in endosomal vehicle. Subsequently, nRAGeD is released from endosomes, possibly due to the proton sponge effect to the cytosol. In the cytosol, siRNA forms the RISC complex and successfully knocks down mutant KRAS.

The inventors synthesized a targeted nRAGeD as an effective siRNA delivery system which can sensitize the KRAS mutant tumor cells to gefitinib if KRAS siRNA is used in nRAGeD. Camouflaging siRNA between gelatin and antibody molecules in nRAGeD increases the stability of the siRNA. Indeed, serum stability and cytoplasmic delivery of siRNA present within nRAGeD are attributed to the synergistic effect of both Gel NP and an antibody. The release of encapsulated gefitinib from nRAGeD primarily governed by degradation of gelatin matrix of the nanoparticle. However, exposure or release of siRNA to form the RNA-induced silencing complex (RISC) can occur in two ways, either through the surface degradation of Gel NP that subsequently releases Ab-siRNA conjugate forming RISC or via direct complexation of RISC with siRNA present on the nanoparticle, as shown in FIG. 23.

Treatment with nRAGeD results in downregulation of pMEK present in the RAS pathway. In comparison with untreated cells, the relative down regulation of pMEK is found to be at least 2 times lower when we used nRAGeD. The downregulation of the downstream proteins mediated by nRAGeD showed a similar response as that of transfected siRNA. Gel NP without siRNA has no effect on pMEK, thereby proving that knocking down the KRAS oncogene effectively decreases the RAS functioning pathway.

The RAS/MEK/ERK pathway is closely associated to PI3K/AKT pathway. With 802 interactive proteins involved in the PI3K signaling and over 2000 proteins in the case of MAPK pathway, several cross talk points exist between PI3K/AKT and RAS/MAPK pathway. Among these proteins, Grb2 associated binder-1 (GAB 1) has been previously identified as an important adaptor protein playing central role in various cell responses. Specifically, GAB 1 is found to be functionally active docking protein for several downstream signaling pathways including EGFR. PI3K and GAB 1 share intrinsic association via tyrosine domain phosphorylation of GAB 1 on SHP2 binding motifs. SHP2 negatively regulates PI3K activation through dephosphorylation of GAB 1 phosphotyrosinases facilitating the activation of RAS for certain cases. In others, activated ERK results in phosphorylation of GAB 1 (Grb2 associated binder 1) on serine and threonine residues adjacent to p85 PI3K binding sites and the nature of signaling dictates regulation levels of GAB-p85 PI3K complexes to control PI3K activity.

In the case of H23 cells, pAKT is reduced with downregulation of pMEK and pERK. The result suggests that the feedback loop of MAPK with PI3K is possibly governed by GAB 1 phosphorylation on serine and threonine residues and not via SHP2-PI3K binding prior to RAS oncogene knockdown. The silencing of activated ERK signaling by RAS oncogene knockdown disrupts the formation of GAB-P85 PI3K complex by negatively affecting serine and threonine phosphorylation levels of GAB 1. This negative feedback results in arresting PI3K pathway and downregulating AKT activity in the case of H23 cells. The fact that HGF is highly expressed in the case of H23 cells strengthens our claims that ERK induces positive regulation of GAB 1 for associating with P85-PI3K via HGF mediation under normal conditions, disruption of which deactivates the PI3K/AKT pathway.

Surprisingly, no effect on cell viability with 100% cell survival is observed with disruption of the RAS/MEK/ERK pathway post RAS oncogene knockdown (for both cell transfected with siRNA or Gel NP without gefitinib). Addition of gefitinib to siRNA treated cells, however, shows a considerable effect on the viability of cancer cells, more so for the nRAGeD compared to transfected siRNA.

One question that still needs to be addressed is the functional mechanism of the H23 cells for survival with knocked-down RAS oncogene, and in effect, with arrested the MAPK and PI3K pathways. Tyrosine phosphorylation of GAB 1 can effectively associate with EGFR. With inability of GAB 1 to form complexes with p85 PI3K due to loss in serine phosphorylation, GAB 1 can effectively regulate EGFR signaling through several positive feedback loops. One possibility is that association of GAB 1 with EGFR by recruiting SHP2 and cascading EGFR downstream signaling. In the case of downstream EGFR, SHP2 is activated by complexing with phosphorylated GAB 1 that binds with EGFR through Grb2. Tyr 627 domain is one of the predominant domains of pGAB1 wherein the complexing occurs. Indeed, Western blot results indicate an increase in pGAB1 (Tyr 627) after oncogene knockdown by TBN supporting our hypothesis that knockdown of KRAS oncogene arrests the MEK/ERK pathway, triggering a feedback loop wherein GAB1 dephosphorylation on serine and/or threonine residues occur, resulting in abrogation of AKT activity.

The stimulation cascades to phosphorylation at tyrosine domains of GAB 1 that induces association of GAB 1 to EGFR through SHP2 recruitment. It is thus possible that the adopted effector pathway of survival post oncogene knockdown is governed through EGFR downstream signaling via disrupted MAPK pathway. It is noteworthy to mention that SHP2 regulation has intrinsic relation with tyrosine kinase inhibitors. Impaired SHP2 functioning or altered localization of SHP2 causes sensitivity to gefitinib. The results suggest that alteration of SHP2 localization caused by recruitment through GAB1 causes disruption of EGF downstream signaling. Addition of gefitinib impairs the functioning of SHP2 and disables complex formation with GAB1, thereby abrogating the already disrupted MAPK pathway, leading to apoptosis of cells, as shown in FIGS. 24A and 24B which show the effect of siRNA and gefitinib on the downstream protein regulation mechanism.

Figures 24A, 24B:
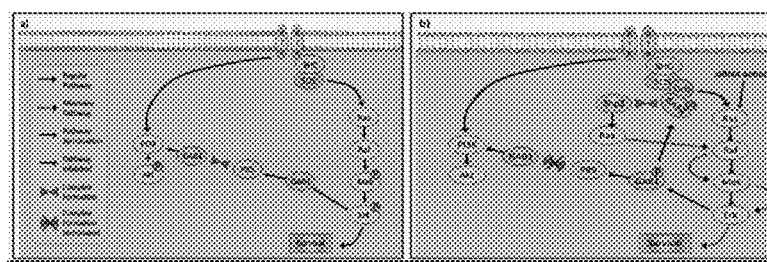
FIGS. 24A-24C are a schematic depicting the effect of siRNA and gefitinib on the downstream protein regulation mechanism.
Figure 24C:
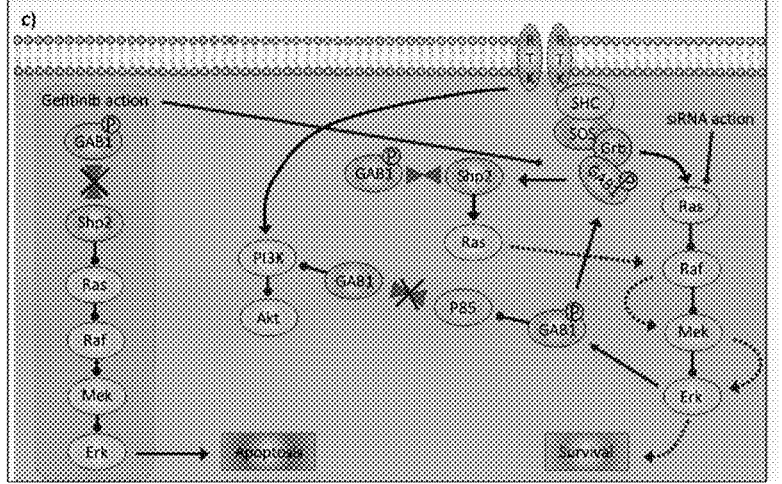

In FIG. 24A, the effector pathway in the presence of oncogenic RAS mutation in H23 cells is shown. In FIG. 24B, the disruption of RAS downstream through siRNA mediated oncogene knockdown affects regular functioning of the RAF/MEK/ERK pathway leading disrupted functioning through MAPK pathway caused by alerted localization of impaired SHP2. In FIG. 24C, addition of gefitinib impedes the recruitment of SHP2 by GAB1 leading to the abrogation of the already disrupted MAPK pathway and eventual apoptosis of the affected cells.

Transfected siRNA may serve as a positive control in terms of oncogene knockdown but a negative control for EGFR blocking. Conversely, a nanoparticle without siRNA may serve as a positive control for EGFR blocking and as a negative control for oncogene knockdown. Understanding the effect of CETUXIMAB™ may further explain the underlying mechanism.

DUSP6 is a cytoplasmic gene that plays a pivotal role in the spatiotemporal mechanism of ERK signaling. The downregulation of DUSP6 is possibly due to inhibition of ERK based on several negative feedback mechanisms. Indeed, siRNA mediated knockdown affects the ERK pathway leading to the regulation of cytoplasmic genes. However, the effect of EGFR signaling on the gene regulation levels post oncogenic loss need to be monitored.

CD73 is a 70 kDa cell surface protein that plays an important role in physiology and pathophysiology of cells. CD73 expression levels remain unchanged with siRNA knockdown mediated by routine transfection as well as for cells transfected with Ab-GelGEFNP with and without siRNA. The result is in agreement with those obtained through protein regulation studies, since the mere knockdown using siRNA causes no impedance to EGFR causes no change in cellular mechanism operating under RAS/MAPK pathway, and therefore are independent of EGFR signaling. However, cells transfected with the TBN are rendered susceptible to change in mechanism as well as EGFR dependent signaling causing imbalance of receptor tyrosine kinases.

For balancing the requisite EGFR expression, CD73 is overexpressed to compensate for the loss of EGFR caused by the nanoparticle. It is evident that standalone siRNA and cetuximab do not influence CD73 expression levels. Correlating these results, increased level of CD73 activity suggests a synergistic effect of CETUXIMAB™ and oncogene knockdown. In the case of siRNA transfected cells, albeit there was loss of activity in RAS pathway, a parallel effector pathway governed by EGFR may have been adopted by the cells for survival. However, the nanoparticles experience EGF receptor mediated endocytosis for siRNA delivery, subsequent oncogene knockdown accompanied with loss of activity in the primary effector pathway. The simultaneous disruption of several interdependent pathways and downstream effector proteins, i.e. RAS/MEK/ERK, PI3K/AKT, GAB1 and SHP2, may be the reason for significant change in cellular gene and protein expression levels leading to sensitization towards small molecule tyrosine kinase inhibitor.

nRAGeD comprising siRNA conjugated to an antibody surface functionalized on gelatin nanoparticles carrying a small molecule tyrosine kinase inhibitor, is highly suitable for the siRNA mediated therapy. Interestingly, the platform protects siRNA from degradation and targets the delivery of siRNA to the desired biomarker on the cancer cell. Also, the gelatin nanoparticles, used as the carrier system, enable concomitant delivery of a drug within the cells of interest. The platform allows loading predetermined and proportional amounts of an antibody, siRNA and drug within the gelatin nanoparticle carrier for effective targeting and high bioavailability.

Using nRAGeD as a therapeutic drug, the inventors have determined that GAB1 plays a crucial role in the absence of gefitinib for cell survival even after oncogene knockdown. The inventors also found that mutant KRAS oncogene knockdown impairs and alters the localization of SHP2, abrogating its complex formation with GAB1 in the presence of gefitinib leading to the apoptosis of the affected cells.

The invention will be now described in more detail by the way of the following non-limiting examples.

EXAMPLE 1

Synthesis of nRAGeD Nanoconjugates

A two-step desolvation process was used to prepare gelatin nanoparticles. 500 mg of gelatin type A (bloom 300) was first dissolved in 10 ml of De-Ionized (DI) Water at 50° C. and subjected to first desolvation using rapid addition of acetone (20 ml). The precipitate was dissolved in 10 ml of DI water (pH2.75) and second desolvation using dropwise addition of acetone (3 ml/min) was initiated. Transformation of the transparent solution to a milky white solution indicated successful desolvation and formation of nanoparticles.

After 10 minutes, the nanoparticles were cross-linked with 200 μl of 25% glutardehyde. The reaction was allowed overnight at 50° C. and the resulting nanoparticulate solution was washed 5 times with DI water to remove excess glutaraldehyde (20,000 g for 45 minutes per wash).

For preparation of gefitinib encapsulation, 1 mg of gefitinib hydrochloride dissolved in DI water was added during the second desolvation process prior to acetone addition. The nanoparticles were then resuspended in DI water and stored at 4° C.

For CETUXIMAB™ conjugation, the carboxyl groups present on the surface of the GelNPs and Gel(Gef)NPs were activated using the EDC/NHS reaction. 10 mg of gelatin nanoparticles were suspended in MES buffer (pH 4.5) at a concentration 5 mg/ml. Activation was performed at room temperature for 3.5 hours under constant shaking (850 RPM). The activated nanoparticles were washed to remove excess EDC/NHS (20,000 g for 20 minutes).

The activated nanoparticles were resuspended in 2 ml PBS (pH 6.7-7.0) containing 600 ul of CETUXIMAB™ (2 mg/ml) for conjugating the antibody on the surface of the nanoparticles to form CETUXIMAB™ conjugated GelNPs (Ab-GelNPs or Ab-Gel(Gef)NPs). The pH of the solution was maintained at 7. The excess antibody was removed through centrifugal separation. The supernatant and the precipitate dispersed in PBS were analyzed for antibody quantification using the Bradford assay with appropriate controls.

For siRNA functionalization, 7 mg of Ab-GelNPs (or Ab-Gel(Gef)NPs) were suspended in RNAse free water (pH 7) and sonicated for few seconds for homogeneous resuspension. 100 ug of Sulfo-SMCC was added to the solution and the reaction was allowed for 3 hrs at room temperature. Post conversion of lysine residues on antibody with the SMCC linker, 50 ul of 50 uM thiol-siRNA, such as for example KRAS G12C thiol-siRNA, was added to the solution for linking the maleimide end of the linker to the thiol end of the siRNA to form nRAGeD.

KRAS G12C siRNA was obtained by annealing equal molar amounts of the sense oligonucleotide with SEQ ID NO. 1 with the antisense oligonucleotide with SEQ ID NO. 2 in PBS buffer. KRAS G12C siRNA was functionalized with a sulfide (S—S) moeity, thereby providing KRAS G12C thiol-siRNA.

AXL siRNA was obtained by annealing equal molar amounts of the sense oligonucleotide with SEQ ID NO. 3 with the antisense oligonucleotide with SEQ ID NO. 4 in PBS buffer. AXL siRNA was functionalized with a sulfide (S—S) moeity, thereby providing KRAS G12C thiol-siRNA.

The excess sulfo-smcc was removed by washing with RNAse-free water prior to siRNA addition. Cy5-labelled siRNA was used for quantifying conjugation efficiency of siRNA to the antibody present on Ab-GelNPs (or Ab-Gel (Gef)NPs) using florescence spectroscopy. The nanoconstruct precipitate after conjugation with siRNA was washed and dispersed in RNAse-free water.

EXAMPLE 2

Characterization of nRAGeD Nanoconjugates

Direct estimation of the amount of gefitinib encapsulated within the nanoparticles was carried out using absorption spectroscopy. 1 ml of the synthesized nanoparticles containing 1 mg/ml of gelatin nanoparticles was completely degraded using 2 mg/ml of protease. The degraded solution was centrifuged at 20,000 g for 30 minutes to ensure no precipitation of particles. The solution was then passed through 10 KDa Amicon filters (10000 g for 10 minutes) the filtrate was characterized for determining the Gefitinib content using absorption spectroscopy at 331 nm. The gefitinib standard curve was then used to determine the concentration of the analyzed filtrate.

Determination of the encapsulation efficiency of gefitinib within the nanoparticles and percent drug loading was characterized using UV-Vis spectroscopy as reported earlier for gefitinib and GelNPs. Gel(Gef)NPs at concentration of 2 mg/ml dispersed in DI water was subjected to protease degradation. The translucent solution turned transparent after 1 hr indicating collapse of gelatin nanoparticles. To ensure that the particles are completely degraded, the solution was centrifuged at 20,000 g for 20 mins and absence of a nanoparticulate precipitate indicated complete degradation of the matrix. The solution was then passed through 0.2 μm filter and the filtrate was analyzed for characteristic 331 nm absorption peak. Gefitinib calibration curve was used as reference. Analysis revealed 40% encapsulation efficiency with 5 μg of gefitinib per mg of Gel(Gef)NPs.

Monoclonal Antibody, CETUXIMAB™, was conjugated to the surface of GelNPs or Gel(Gef)NPs. The lysine moiety present on the antibody was used to link with the carboxyl groups present on the gelatin. The amount of antibody conjugated to the nanoparticles was determined using the Bradford Assay. It was determined that 45 (±5) μg of cetuximab was present on the surface of the nanoparticles. The percentage of antibody conjugation changed proportionally with the relative initial amount of GelNPs for all 5 experiments carried out for reproducibility (amount of CETUXIMAB™ was kept constant at 600 μg).

However, normalization of an antibody conjugated with per mg of Gel NPs remained constant at 45 (±5) g per mg of Gel NPs. The hydrodynamic size of the antibody conjugated nanoparticles did not show any significant change and was determined to be 210 nm. See FIG. 4. TEM images however appeared relatively well resolved in the case of Ab-Gel(Gef) NPs compared to Gel(gef) NPs, as shown in FIG. 7. This could be due to the increase of the surface density of the nanoconstruct leading to a relatively higher contrast for the Ab-Gel NPs compared to GelNPs. The $\zeta$ of Ab-GelNPs or Ab-Gel (Gef) NPs (in DI Water), however, showed a drastic change post surface modification. The $\zeta$ changed to −12 mV from +18 mV confirming nanoparticle surface alteration. See FIGS. 5 and 6.

Figures 8A, 8B, 8C:
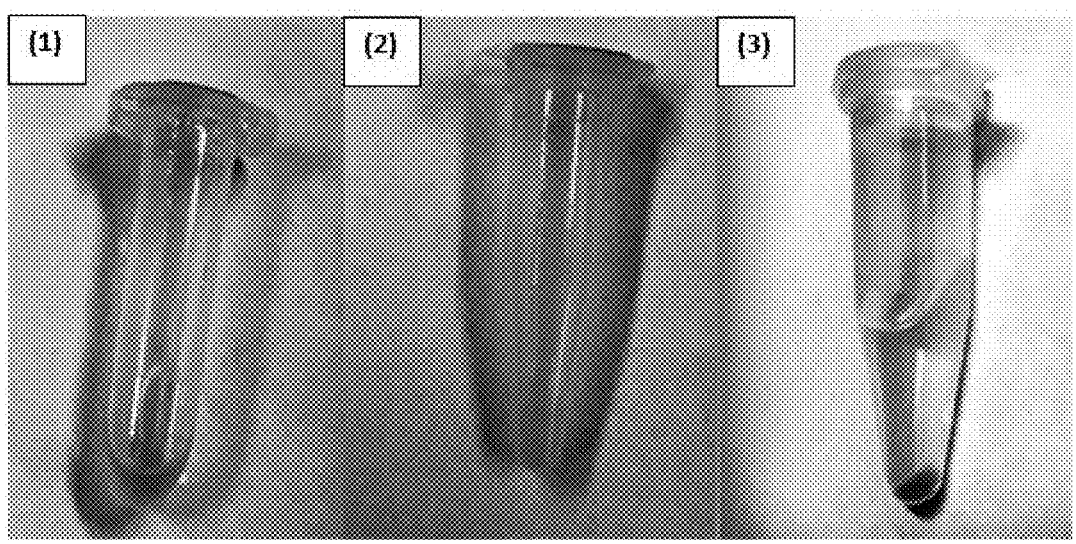
FIGS. 8A-8C reprot siRNA loaded on nRAGeD by visual observation of a significant increase of the amount of siRNA labeled with Cy5 on nRAGeD (FIG. 8C) in comparison to siRNA solution (FIG. 8A) and Ab-Gel-nanoparticles (FIG. 8B).

Estimation of siRNA loaded on the nanocomplex was carried out using absorption spectroscopy. The supernatant of complex after centrifugation (20,000 g, 20 mins) was analyzed for characteristic 280 nm peak of siRNA using UV-V is absorption spectroscopy and percentage of siRNA bound to the nanoparticle was determined to be 98 (±1) %. To ensure the high functionalization efficiency, cy5-labeled siRNA was used to determine the conjugation efficiency using florescence spectroscopy. Post centrifugal separation, the suspension was subjected to fluorescence spectroscopy with emission at 670 nm. Using the manufacturer's Extinction coefficient (367,569 L·mol$^{-1}$·cm$^{-1}$), the fluorescence signal obtained was consistent with earlier results and revealed ~98.5% conjugation. The supernatant had negligible fluorescence signal. Visual observation of characteristic blue color of Cy5 present on the nanoconstruct pellet and absence of the color in the supernatant also confirmed the high siRNA conjugation as shown in FIG. 8A showing cy-siRNA solution in comparison to Ab-Gel-NP solution of FIG. 8B and nRAGeD in FIG. 8C.

Absolute number of si RNA, antibodies and TKIs per GelNP is listed in Table 1.

TABLE 1

Concentration of which component comprising nRAGeD

| Constituent | Mass (μg) | μmol. | Constituent | Absolute Number |
|---|---|---|---|---|
| Gelatin | 1000 | 1 | No. of Gelatin NP | 1 |
| Gefitinib | 5 | 1 | No. of Gefitinib | ~13500 |
| antibody | 50 | 0.03 | No. of Cetuximab | ~350 |
| siRNA | 13 | 0.1 | No. of siRNA | ~475 |

Stability of siRNA in the nRAGeD nanoconjugate was analyzed by using SDS-PAGE gel electrophoresis. The nanoparticles with appropriate controls including naked siRNA, gelatin nanoparticles and CETUXIMAB™ were subjected to a 10% serum solution. At predetermined time intervals (0, 0.5, 1, 2, 4, 8 and 24 hr), the suspension were aliquoted and refrigerated at −50° C. The solutions were then subjected to SDS-PAGE and presence of siRNA was detected using nucleic acid staining dye GelRed.

The use of the thio-ether bond for complexing siRNA to the antibody present on the gelatin nanoparticles renders it uncleavable from the nanoconstruct. Any gelatin degradation agent such as protease or antibody disruption would have adverse effect on siRNA quality. Therefore, the stability study of the siRNA was based on the direct GelRed nucleic acid staining of the siRNA present on the nanocomplex.

For in vitro stability studies, an aliquot of each sample containing 75 pmoles of siRNA was analyzed by 4-15% polyacrylamide gel electrophoresis (PAGE, BioRad, 100V for 60 minutes) using Tris borate EDTA running buffer. The gels were then stained with GelRed (Thermo Scientific, USA) and imaged using UV trans-illumination light filter and image analysis was performed using Biorad Laboratories Image Lab v.3.0.

As shown in FIG. 9A, a time related serum stability analysis using SDS-PAGE reveals highly stable siRNA present on the nRAGeD. The lane description for FIG. 9 is as follows: 1-0 hr, 2-0.5 hr, 3-1 hr, 4-2 hr, 5-4 hr, 6-12 hr, 7-24 hr and 8-naked siRNA at 0 hr in DI water. The lower band in lane 1 corresponds to free siRNA and siRNA cleaved from nRAGeD by serum solution. The band disappears within 30 mins indicating the short stability of free siRNA in serum.

As also shown in FIG. 9A, unbound or electrostatically bound nanoparticles had degradation profile similar to naked siRNA. However, siRNA chemically bound to nRAGeD were highly stable with minimal degradation for 24 hrs. siRNA sandwiched between antibody and gelatin nanoparticle or siRNA engulfed within antibody is protected from serum enzymes. An antibody, with a molecular weight of 152 KDa can completely mask and protect the relatively small 14 KDa oligonucleotide.

In addition, a 30-day stability analysis of the nanoparticle stored at −50° C. showed minimal degradation (FIG. 9B). In vitro stability studies of nRAGeD as analyzed by hydrodynamic size in biological media containing 10% serum showed no significant variations in the diameter of the nanoparticles until 24 hr time points (FIG. 9C).

EXAMPLE 3

Treatment of Cancer Cells with nRAGeD Nanoconjugates

To understand the cellular internalization capability, Gel NP encapsulated with fluorescein (fl) dye (GelflNP) and siRNA labeled with cy5 dye (siRNAcy5) were used for detection with two different fluorescent signals. The internalization study was performed in the KRAS mutant H23 non-small cell lung cancer cell line. The internalization was analyzed using fluorescence microscopy (FIG. 10).

The H23 cells were incubated with various analogues of the nanoconjugate. For simplicity, dyes, Fluorescein (fl) and Cy5 (cy5) functionalized to the corresponding ingredient of the nanoparticle is depicted through subscript. The various analogues are as follows: (1) GelflNP-Ab-siRNAcy5, (2) $Gel_{fl}$NP-Ab-siRNA, (3) Gel NP-$Ab_{cy5}$-siRNA, (4) GelNP-Ab-$siRNA_{cy5}$, (5) $siRNA_{cy5}$ and (6) $Ab_{cy5}$. H23 cells were seeded in 6-well plates ($5\times10^5$ cells/well). Cells were grown on a poly-L-lysine treated glass coverslip. 100 ul of each samples (Analogues 1, 2, 3, 4 and 5) were incubated for 4 hours at 37° C. in serum free media. After treatment, resulting cover slips were washed with PBS (1×) to remove unbound particles and microscopic slides were prepared with DAPI nuclear stain. Slides were imaged using a polarized dark-field fluorescence microscope at 20× and recorded.

Figure 10:
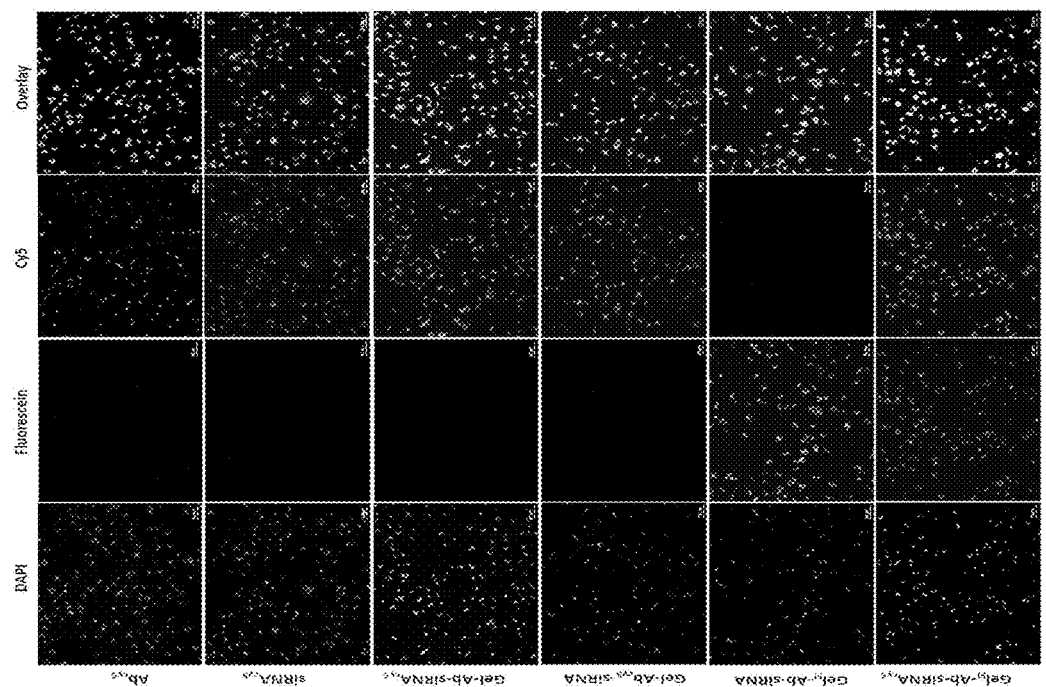
FIG. 10 is florescence microscopy images of H23 cancer cells incubated with nRAGeD ($Gel_{F1}Ab$-$siRNA_{Cy5}$) or its analogues $Gel_{F1}Ab$-siRNA, Gel-$Ab_{Cy5}$-siRNA, Gel-AbsiRNA$_{Cy5}$, siRNA$_{Cy5}$ and Ab$_{Cy5}$. DAPI was used as a nuclear staining marker. Fluorescein is incorporated into nanoparticles. Cy5 is used for labelling an antibody and siRNA.

As shown in FIG. 10, co-localization of siRNAcy5 and GelflNP was confirmed by two fluorescence signals emanating from cells. The figure shows co-localization of cy5 labelled siRNA and fluorescein encapsulated gelatin nanoparticles in H23 cells. Appropriate controls with and without fluorescein or cy5 were used. All images were recorded at 20× magnification. This confirms that nRAGeD delivers its drug load to cancer cells.

To estimate the relative amount of siRNA internalization within cells, a flow cytometry analysis was performed.

H23 cells were independently incubated with (i) siRNAcy5 along with transfecting agent (TA-siRNAcy5); (ii) Gel NP-Ab-siRNAcy5; or (iii) Ab-siRNAcy5 for 4 hours (FIG. 11). After 4 hours, the cells were repeatedly washed to remove surface adhered molecules and were trypsinized. Subsequently, the cells were analyzed using flow cytometry and the results showed internalization in the following order: Gel NP-Ab-siRNAcy5>TA-siRNAcy5>Ab-siRNAcy5. The amount of siRNA internalized through was at least two fold higher than transfected siRNA (FIG. 11). The results showed that nRAGeD is as an effective siRNA delivery system.

It is important to ensure that internalized nanoparticle is present in the cytoplasm and knocks down the KRAS gene as intended and regulates the appropriate protein levels. In order to understand downstream protein level regulation before and after oncogene knockdown, H23 cell line harboring KRAS mutation at G12C was used.

The effect of nRAGeD on the RAS/RAF/MEK/ERK cascade was studied. Untreated H23 cells exhibit phosphorylated downstream proteins in two effector pathways. In first pathway, RAS activates downstream effector enzymes enabling cell proliferation and survival through phosphorylation of RAF. This phosphorylation in-turn activates mitogen activated protein kinase (MEK/MAPK) that is responsible for activation of ERK. In second effector pathway, RAS has been found to activate PI3K effector pathway leading to phosphorylated AKT.

Figures 12A, 12B:
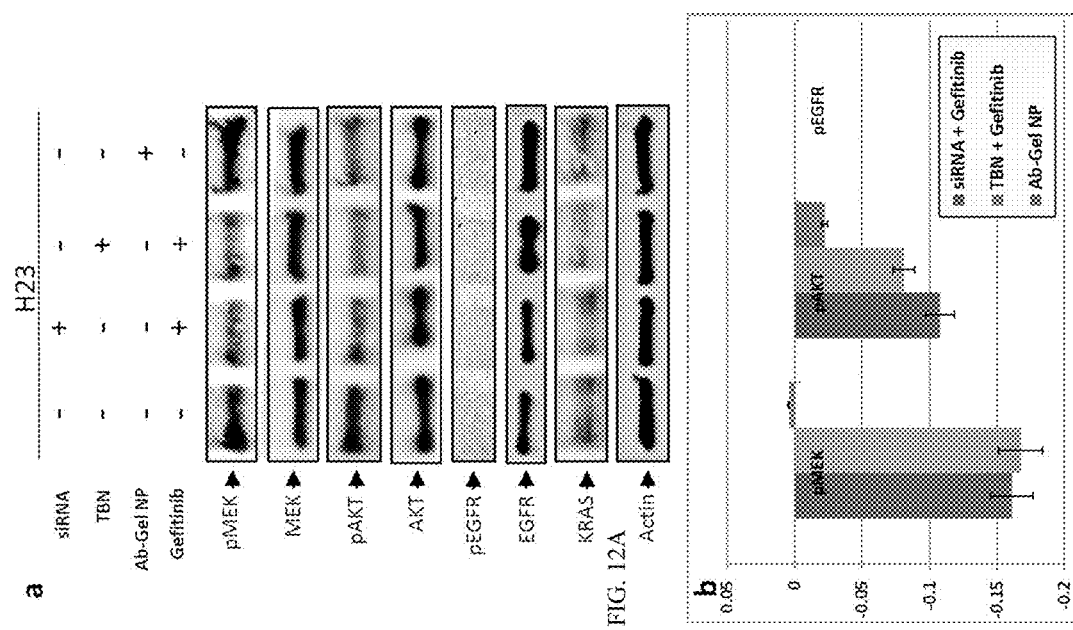
FIG. 12A is a Western blot analysis of protein expression in cancer cells treated with nRAGeD.
FIG. 12B is a densitometry analysis of the data from FIG. 12A.

The PI3K/AKT signaling network that runs parallel to RAS/MAPK pathway is known to have several points of interaction with each other influencing inter-signal transduction. The disruption of RAS signaling with oncogene knockdown results in downregulation of primary downstream protein pMEK as well as parallel pathway protein pAKT. The results indicate a direct intrinsic relation between the two pathways primarily governed by RAS as shown in FIGS. 12A and 12B by Western Blot analysis. FIG. 12a is a Western Blot analysis which shows expression of proteins pMEK, MEK, pACT, AKT, pEGFR, EGFR and KRAS in H23 cancer cells treated with nRAGeD in comparison to H23 not treated or treated with KRAS siRNA alone. As reported in FIG. 12B, a significant downregulation of phosphorylated MEK and AKT is observed in cancer cells treated with nRAGeD.

The Western blot analysis was performed as follows. Cells were seeded at a density of $1\times10^6$ cells/ml and incubated for overnight at 37° C. in 5% $CO_2$ atmosphere. Nanoparticle and relevant control samples were incubated in serum free media for the period of 72 hrs. For control experiments, siRNA transfection (240 nM) was performed using TransIT-X2 dynamic delivery system transfecting agent (Mirus Bio) as per manufacturer's instructions. Whole-cell lysates were prepared using Triton X 100 lysis buffer with MS-SAFE protease and phosphatase cocktail inhibitor (Sigma-Aldrich) and the protein concentration was equalized by Bicinchoninic acid assay (Sigma-Aldrich). Proteins were separated by 4-15% SDS-PAGE (Bio-Rad) and were transferred onto nitrocellulose membranes (GenScript).

Membranes were incubated with primary antibody overnight, were washed and incubated with secondary antibody. Primary antibodies used for western blotting are rabbit polyclonal anti-β-actin, rabbit monoclonal anti-AKT, rabbit monoclonal anti-phospho-AKT, rabbit polyclonal anti-MEK1/2, rabbit polyclonal anti-phospho-MEK1/2, rabbit monoclonal anti-EGFR, rabbit monoclonal anti-phospho-EGFR, rabbit monoclonal anti-SHP2, rabbit polyclonal anti-phospho-SHP2 (Tyr542), rabbit polyclonal anti-phospho-SHP2 (Tyr580), rabbit monoclonal anti-phospho-GAB1 (Tyr627), rabbit polyclonal anti-phospho-GAB1 (Tyr307), all from Cell Signaling and mouse monoclonal anti-KRAS from Santa Cruz Biotech. The membranes were developed with peroxidase-labeled anti-mouse or anti-rabbit IgG (Cell Signaling Tech.) using enhanced chemiluminescence substrate (Pierce) and imaged on Fujifilm LAS-3000 imaging system. Actin protein levels were used as a control for adequacy of equal protein loading. Protein expression levels were quantified by densitometry analysis.

Figure 13:
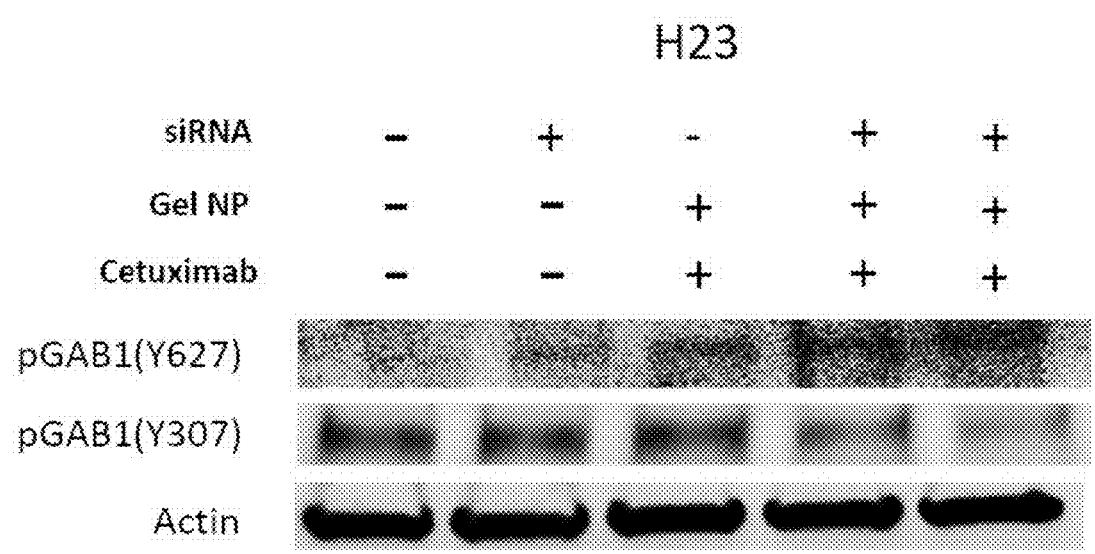
FIG. 13 is a Western blot analysis for phosphorylated forms of pGAB1 (Y627) and pGAB1 (Y307).

Additional Western blot analysis was performed to detect phosphorylation of GAB1. As shown in FIG. 13, GAB1 and pGAB1 at Tyr 627 was found to be upregulated upon treatment with nRAGeD while no substantial difference was found for pGAB1-307.

Figure 14A:
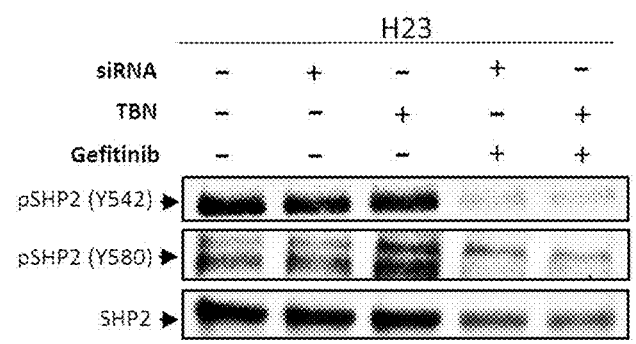
FIG. 14A is a Western blot analysis of SHP2 protein and its phosphorylated forms.
Figure 14B:
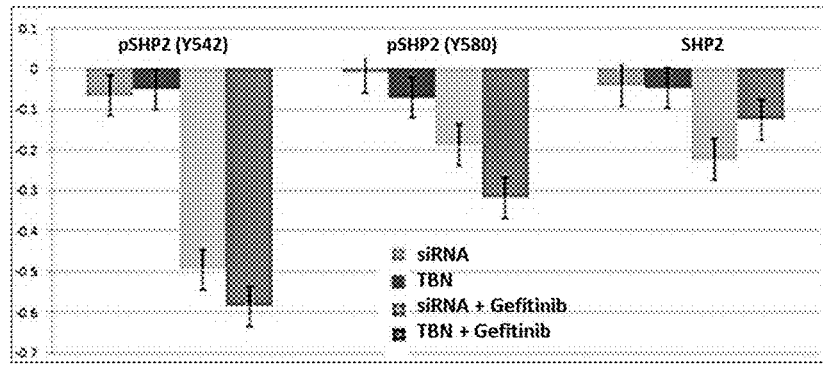
FIG. 14B is a densitometry analysis of the Western blot of FIG. 14A.

Another Western blot analysis was performed for SHP2, pSHP2 (Y542) and pSHP2 (Y580) as shown in FIGS. 14A and 14B. As shown by Western blot (FIG. 14A) and calculated by its densitometry analysis (FIG. 14B) SHP2, pSHP2 (Y542) and pSHP2 (Y580) remained unchanged after treatment with Gel NP (without gefitinib). However, a significant downregulation was found in the presence of gefitinib for the cells transfected with siRNA or treated with nRAGeD. In FIG. 14A, treatment on KRAS mutated H23 cells was performed by either transfecting cells with siRNA or by delivering siRNA using a gelatin nanoparticle not loaded with gefitinib did not show any effect on SHP2 and p-SHP2. However, in the presence of gefitinib, pSHP2 (Y542), pSHP2 (Y580) and SHP2 protein were downregulated indicating impaired SHP2 function—a probable cause of H23 cell apoptosis after oncogene knockdown. This result is confirmed by the densitometry image analysis of FIG. 14B using BioRad Image lab V.3 was carried out to quantify the proteins.

Figure 15:
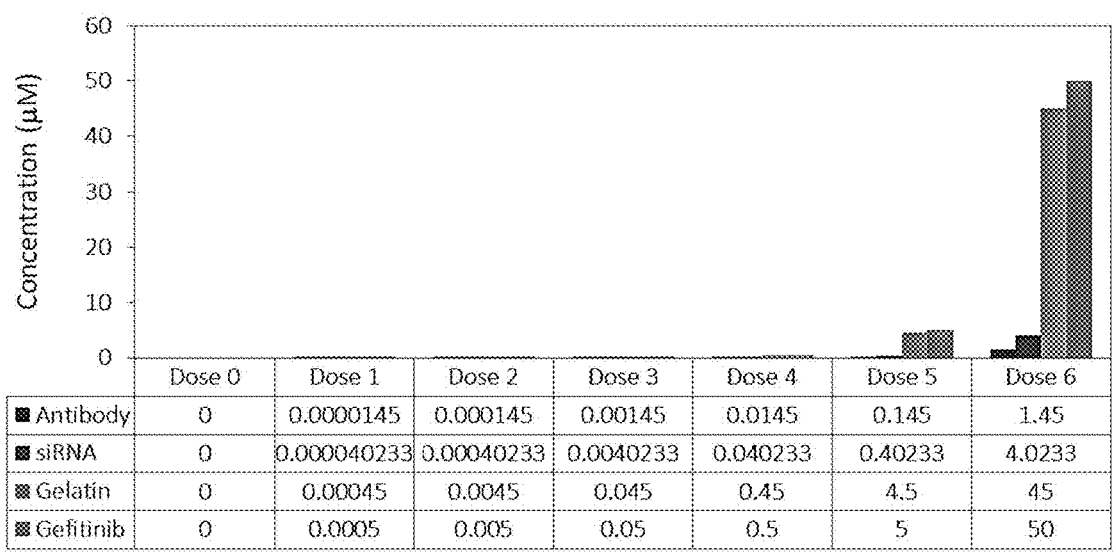
FIG. 15 reports the MTT dose concentration of nanoparticles and its various analogues used for the in vitro toxicity in lung cancer cells.

Considering downregulation of downstream-phosphorylated proteins, the cell viability of H23 cells (MTT assay) after knocking down the RAS pathway was then investigated. For comparison of various individual components of the nanoparticle, the cell toxicity data was normalized with gefitinib concentration and the corresponding concentration of appropriate controls are shown in FIG. 15.

The IC50 value of gefitinib for H23 cell line was determined to be 50 µM. Interestingly, transfected siRNA (4 µM, dose corresponding to 50 µM gefitinib) did not cause any cytotoxicity and the viability of cells remained 100%, suggesting oncogenic disruption alters the effector pathway, but does not lead to apoptosis.

When nRAGeD was used, the IC50 value drastically reduced by 20 fold to 2.5 µM, and complete loss of cell viability was found for nanoparticle containing 5 µM of gefitinib, as shown in FIG. 16 which shows the cell viability of the nanoparticles at 5 µM gefitinib concentration was 5% compared to 25% viability for cells transfected with siRNA followed by gefitinib treatment.

This in vitro cytotoxicity analysis was performed according to the following protocol. H23 human adenocarcinoma non-small cell lung cancer cells (ATCC, USA) and A549 human adenocarcinoma epithelial cells (ATCC, USA) were grown in RPMI 1640 medium supplemented with 4.5 g/L D-glucose, 25 mM HEPES, 0.11 g/L sodium pyruvate, 1.5 g/L sodium bicarbonate, 2 mM L-glutamine, 10% heat-inactivated fetal bovine serum (Altlanta Biologicals, USA) and 0.1% v/v gentamycin.

Cells were cultured in a humidified atmosphere of 95% air and 5% $CO_2$ at 37° C. (Thermo Scientific, USA). For determining in vitro cytotoxicity, the MTT assay was performed by incubating various samples including the nanoparticle of interest on H23 and A549 cells.

The concentrations were normalized with respect to gefitinib concentration for all samples (50 µM, 5 µM, 0.5 µM, 0.05 µM, 0.005 µM and 0 µM). For samples that did not contain gefitinib, weight of gelatin nanoparticles was used for normalization. Each sample was analyzed in triplicate. After 24 hours of incubation, 10 µl of MTT solution (ATCC, USA) was added and the plate was incubated at 37° C. for 4 hours. Crystals formed were dissolved in 100 µl solubilizing buffer and the plates were kept at 25° C. for 2 hours. The intensity of the color developed after addition of the solubilizing buffer was measured using Biotek Cytation 3 spectrophotometer at 570 nm.

Viability of the cells transfected with various samples was then calculated by considering the untreated cells as 100% viable.

The controls used for cytotoxicity assay include gefitinib, transfected siRNA with and without gefitinib (siRNA (TA)+gef, siRNA (TA)), cetuximab (Ab), cetuximab-siRNA (Ab-siRNA) with and without gefitinib, gelatin nanoparticles (Gel NP), gefitinib encapsulated gelatin nanoparticles (Gel-GEFNP), and mock siRNA with gefitinib (see FIGS. 15, 17, and 19). No significant changes in cell toxicity relative to nRAGeD were found in the case of controls.

As shown in FIG. 17, in vitro cellular viability data was obtained after treatment with gefitinib, siRNA(TA), siRNA (TA)+Gef, or Ab-siRNA(TA)+Gef on KRAS mutant H23 cells. Transfected siRNA showed no toxicity to the cells. However, cells transfected with siRNA and subsequently treated with gefitinib, exhibited viability of 30% at 5 µM gefitinib concentration. Ab-siRNA conjugate upon transfection and treatment with gefitinib showed cell viability of 5% at 50 µM gefitinib concentration. Results indicated post oncogene knockdown, H23 cells get sensitized toward gefitinib.

As shown in FIG. 18, in vitro cellular viability of individual components of nRAGeD and physical mixture of all components together on H23 cells showed minimal cytotoxicity indicating the toxicity caused specifically by a combination of drugs delivered by nRAGeD in H23 cells. Thus, there is a synergistic effect of drugs provided by nRAGeD.

FIG. 19 reports in vitro cellular viability of H23 cells transfected with mock siRNA followed by treatment with gefitinib. Results indicate minimal change in viability for mock siRNA compared to the viability of cells treated with gefitinib.

Figure 20:
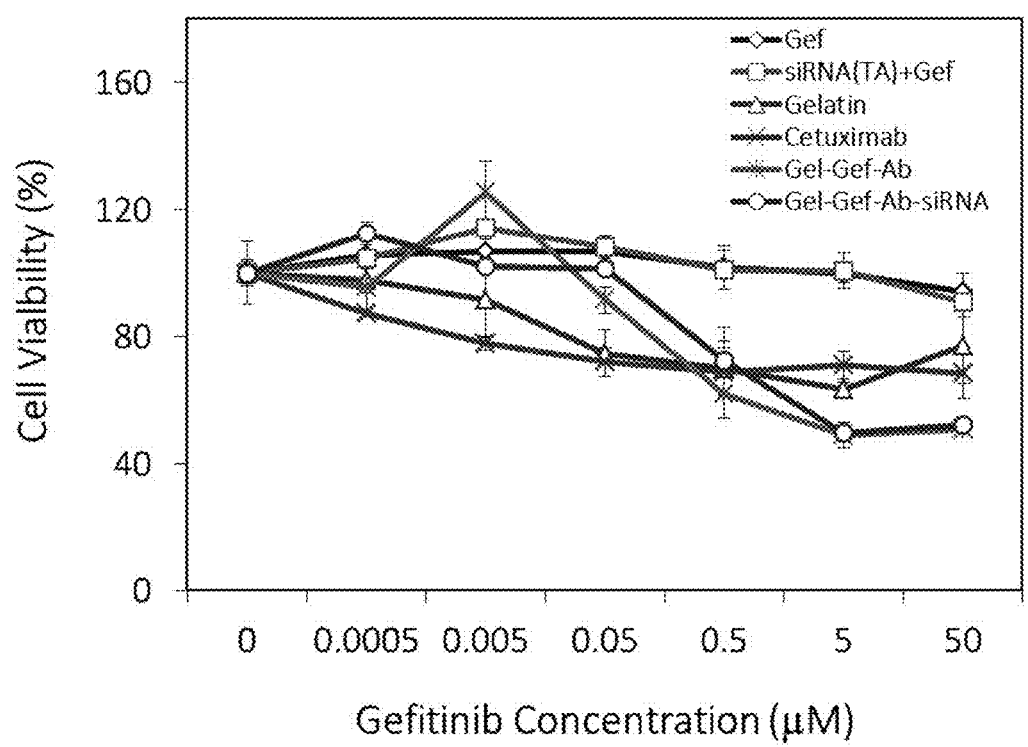
FIG. 20 reports in vitro cellular viability of cancer cells with KRAS G12S mutation treated with nRAGeD carrying RAS G12C si-RNA.

The treatment effect observed in H23 cells was not observed in other epithelial cancer cells A549 which harbor the G12S mutation in KRAS, as shown in FIG. 20. Thus, KRAS G12C siRNA is highly specific for cancers with this particular point mutation.

The effect of the oncogene knockdown on gene expression of DUSP6 and NT5E genes were observed by quantitative real-time RT-PCR. Initially H23 cells (1×106 cells/well) were treated with 4 samples including untreated, GelNP-Ab, GelNP-Ab-siRNA and siRNA (transfection agent). RNA was extracted through standard RNA extraction protocol. cDNA was synthesized from RNA extracted from the treated cells. The quality and the concentration of the extracted RNA was determined using bioanalyzer. 18sRNA was used as an reference gene (housekeeping gene) for data normalization. Primers and probes for all genes were purchased from Integrated DNA Technologies (IDT). PCR was performed in a reaction volume of 20 µl containing 2 µl cDNA using the Gene Amp 7700 Sequence Detection System. The comparative Ct protocol was followed to determine the relative expression levels. These results are shown in FIGS. 22A and 22B.

EXAMPLE 4

Treatment of a Mammal with nRAGeD Nanoconjugates

The safety study was conducted in five normal mice by repeated intravenous (IV) injection of the nRAGeD nanoconstruct (80 mg/Kg body weight) for three consecutive days, followed by euthanasia. During treatment, animals did not show any abnormal behavior. Subsequently, major organs were collected and histopathology was performed. The histology analysis as shown in FIG. 21 indicated no signs of toxicity showing good tolerance for nRAGeD nanoconjugates.

All animal experiments were conducted in accordance with Freimann Life Science Center guidelines for humane animal treatment. In vivo dose safety studies of TBN were performed in normal mice. nRaGeD (80 mg/Kg of body weight) was suspended in PBS and administered via tail vein for 3 consecutive days. Animals were monitored for any changes in behavior and no changes in behavior was noticed. After 3 days, animals were sacrificed and vital organs collected, tissues fixed in formalin, stained with H&E for histology.

REFERENCES

1 Jemal, A., Siegel, R., Xu, J. & Ward, E. Cancer statistics, 2010. *CA: a cancer journal for clinicians* 60, 277-300 (2010).
2 Mao, C. et al. KRAS mutations and resistance to EGFR-TKIs treatment in patients with non-small cell lung cancer: a meta-analysis of 22 studies. *Lung cancer* (Amsterdam, Netherlands) 69, 272-278 (2010).
3 Sunaga, N. et al. Knockdown of Oncogenic KRAS in Non-Small Cell Lung Cancers Suppresses Tumor Growth and Sensitizes Tumor Cells to Targeted Therapy. *Molecular Cancer Therapeutics* 10, 336-346, doi:10.1158/1535-7163.mct-10-0750 (2011).
4 Buyens, K. et al. Liposome based systems for systemic siRNA delivery: Stability in blood sets the requirements for optimal carrier design. *Journal of Controlled Release* 158, 362-370, doi:10.1016/j.jconrel.2011.10.009 (2012).
5 Ding, Y. et al. Gold Nanoparticles for Nucleic Acid Delivery. *Molecular Therapy* 22, 1075-1083, doi:10.1038/mt.2014.30 (2014).
6 Whitehead, K. A., Langer, R. & Anderson, D. G. Knocking down barriers: advances in siRNA delivery. *Nature Reviews Drug Discovery* 8, 129-138, doi:10.1038/nrd2742 (2009).
7 Giljohann, D. A., Seferos, D. S., Prigodich, A. E., Patel, P. C. & Mirkin, C. A. Gene Regulation with Polyvalent siRNA-Nanoparticle Conjugates. *Journal of the American Chemical Society* 131, 2072-2073, doi:10.1021/ja808719p (2009).
8 Oh, Y.-K. & Park, T. G. siRNA delivery systems for cancer treatment. *Advanced Drug Delivery Reviews* 61, 850-862, doi:10.1016/j.addr.2009.04.018 (2009).
9 Gilleron, J. et al. Image-based analysis of lipid nanoparticle-mediated siRNA delivery, intracellular trafficking and endosomal escape. *Nature Biotechnology* 31, 638-646, doi:10.1038/nbt.2612 (2013).
10 Liu, P., Xu, B., Li, J. & Lu, H. BAG3 gene silencing sensitizes leukemic cells to bortezomib-induced apoptosis. *FEBS Letters* 583, 401-406, doi:10.1016/j.febslet.2008.12.032 (2009).
11 Liu, X. et al. Survivin gene silencing sensitizes prostate cancer cells to selenium growth inhibition. *BMC Cancer* 10, No pp given, doi:10.1186/1471-2407-10-418 (2010).
12 Wei, L. et al. Knockdown of cancerous inhibitor of protein phosphatase 2A may sensitize NSCLC cells to cisplatin. *Cancer Gene Therapy* 21, 194-199, doi:10.1038/cgt.2014.18 (2014).
13 Saraswathy M, G. S. Recent developments in the co-delivery of siRNA and small molecule anticancer drugs for cancer treatment. *Materials Today* 17, 298-306 (2014).
14 Aleman, L. M., Doench, J. & Sharp, P. A. Comparison of siRNA-induced off-target RNA and protein effects. *Rna* 13, 385-395, doi:10.1261/rna.352507 (2007).
15 Aksamitiene, E., Kiyatkin, A. & Kholodenko, B. N. Cross-talk between mitogenic Ras/MAPK and survival PI3K/Akt pathways: a fine balance. *Biochemical Society Transactions* 40, 139-146, doi:10.1042/bst20110609 (2012).
16 Yun, C.-H. et al. The T790M mutation in EGFR kinase causes drug resistance by increasing the affinity for ATP. *Proceedings of the National Academy of Sciences of the United States of America* 105, 2070-2075, doi:10.1073/pnas.0709662105 (2008).
17 Baker, N. M. & Der, C. J. Cancer Drug for an 'undruggable' protein. *Nature* (London, United Kingdom) 497, 577-578, doi:10.1038/nature12248 (2013).
18 Rosell, R. et al. Prognostic impact of mutated K-ras gene in surgically resected non-small cell lung cancer patients. *Oncogene* 8, 2407-2412 (1993).
19 Huang, C., Li, M., Chen, C. & Yao, Q. Small interfering RNA therapy in cancer: mechanism, potential targets, and clinical applications. *Expert Opinion on Therapeutic Targets* 12, 637-645, doi:10.1517/14728222.12.5.637 (2008).
20 Ostrem, J. M., Peters, U., Sos, M. L., Wells, J. A. & Shokat, K. M. K-Ras(G12C) inhibitors allosterically control GTP affinity and effector interactions. *Nature* (London, United Kingdom) 503, 548-551, doi:10.1038/nature12796 (2013).
21 Coester, C. J., Langer, K., Von Briesen, H. & Kreuter, J. Gelatin nanoparticles by two step desolvation-a new preparation method, surface modifications and cell uptake. *Journal of Microencapsulation* 17, 187-193 (2000).
22 Balthasar, S. et al. Preparation and characterisation of antibody modified gelatin nanoparticles as drug carrier system for uptake in lymphocytes. *Biomaterials* 26, 2723-2732, doi:10.1016/j.biomaterials.2004.07.047 (2005).
23 Faivre, L. et al. A simple HPLC-UV method for the simultaneous quantification of gefitinib and erlotinib in human plasma. *Journal of Chromatography B: Analytical Technologies in the Biomedical and Life Sciences* 879, 2345-2350, doi:10.1016/j.jchromb.2011.06.026 (2011).
24 Hickerson, R. P. et al. Stability Study of Unmodified siRNA and Relevance to Clinical Use. *Oligonucleotides* 18, 345-354, doi:10.1089/oli.2008.0149 (2008).
25 Alakhova, D. Y. & Kabanov, A. Y. *Drug Delivery in Oncology. From Basic Research to Cancer Therapy.* 3 Volumes. Edited by Felix Kratz, Peter Senter and Henning Steinhagen. Vol. 53 (2014).
26 Derfus, A. M., Chen, A. A., Min, D.-H., Ruoslahti, E. & Bhatia, S. N. Targeted Quantum Dot Conjugates for siRNA Delivery. *Bioconjugate Chemistry* 18, 1391-1396, doi:10.1021/bc060367e (2007).
27 Zugasti, O. et al. Raf-MEK-Erk cascade in anoikis is controlled by Rac1 and Cdc42 via Akt. *Molecular and Cellular Biology* 21, 6706-6717, doi:10.1128/mcb.21.19.6706-6717.2001 (2001).

28 Schmid, K. et al. EGFR/KRAS/BRAF mutations in primary lung adenocarcinomas and corresponding locoregional lymph node metastases. *Clinical cancer research: an official journal of the American Association for Cancer Research* 15, 4554-4560 (2009).

29 Ochi, N. et al. Src mediates ERK reactivation in gefitinib resistance in non-small cell lung cancer. *Experimental Cell Research* 322, 168-177, doi:10.1016/j.yexcr.2014.01.007 (2014).

30 Li, H. et al. Blocking the PI3K/AKT and MEK/ERK signaling pathways can overcome Gefitinib-resistance in non-small cell lung cancer cell lines. *Advances in Medical Sciences* 56, 275-284, doi:10.2478/v10039-011-0043-x (2011).

31 Schneeberger Valentina, E. et al. Inhibition of SHP2 suppresses mutant EGFR-induced lung tumors in transgenic mouse model of lung adenocarcinoma. *Oncotarget* 6, 6191-6202 (2015).

32 Bermudez, O. et al. Post-transcriptional regulation of the DUSP6/MKP-3 phosphatase by MEK/ERK signaling and hypoxia. *Journal of Cellular Physiology* 226, 276-284, doi:10.1002/jcp.22339 (2010).

33 Zhang, Z. et al. Dual specificity phosphatase 6 (DUSP6) is an ETS-regulated negative feedback mediator of oncogenic ERK signaling in lung cancer cells. *Carcinogenesis* 31, 577-586, doi:10.1093/carcin/bgq020 (2010).

34 Zhi, X. et al. Potential prognostic biomarker CD73 regulates epidermal growth factor receptor expression in human breast cancer. *IUBMB Life* 64, 911-920, doi:10.1002/iub.1086 (2012).

35 Giubellino, A., Burke, T. R. & Bottaro, D. P. Grb2 signaling in cell motility and cancer. *Expert Opinion on Therapeutic Targets* 12, 1021-1033, doi:10.1517/14728222.12.8.1021 (2008).

36 Cai, T., Nishida, K., Hirano, T. & Khavari, P. A. GAB1 and SHP-2 promote Ras/MAPK regulation of epidermal growth and differentiation. *Journal of Cell Biology* 159, 103-112, doi:10.1083/jcb.200205017 (2002).

37 Zhang, S. Q. et al. Receptor-specific regulation of phosphatidylinositol 3'-kinase activation by the protein tyrosine phosphatase SHP2. *Molecular and Cellular Biology* 22, 4062-4072, doi:10.1128/mcb.22.12.4062-4072.2002 (2002).

38 Derman, M. P., Cunha, M. J., Barros, E. J. G., Nigam, S. K. & Cantley, L. G. HGF-mediated chemotaxis and tubulogenesis require activation of the phosphatidylinositol 3-kinase. *American Journal of Physiology* 268, F1211-F1217 (1995).

39 Yu, C. F., Liu, Z.-X. & Cantley, L. G. ERK negatively regulates the epidermal growth factor-mediated interaction of GAB1 and the phosphatidylinositol 3-kinase. *Journal of Biological Chemistry* 277, 19382-19388, doi:10.1074/jbc.M200732200 (2002).

40 Chen, J.-T. et al. Cigarette smoking induces overexpression of hepatocyte growth factor in type II pneumocytes and lung cancer cells. *American Journal of Respiratory Cell and Molecular Biology* 34, 264-273, doi:10.1165/rcmb.2005-01170C (2006).

41 Chiang, Y.-Y. Hepatocyte growth factor induces hypoxia-related interleukin-8 expression in lung adenocarcinoma cells. *Molecular Carcinogenesis* 48, 662-670, doi:10.1002/mc.20521 (2009).

42 Hoeben, A., Martin, D., Clement, P. M., Cools, J. & Gutkind, J. S. Role of GRB2-associated binder 1 in epidermal growth factor receptor-induced signaling in head and neck squamous cell carcinoma. *International Journal of Cancer* 132, 1042-1050, doi:10.1002/ijc.27763 (2013).

43 Jeannot, V. et al. The PI3K/AKT pathway promotes gefitinib resistance in mutant KRAS lung adenocarcinoma by a deacetylase-dependent mechanism. *International Journal of Cancer* 134, 2560-2571, doi:10.1002/ijc.28594 (2014).

44 Yuan, T. L. & Cantley, L. C. PI3K pathway alterations in cancer: variations on a theme. *Oncogene* 27, 5497-5510, doi:10.1038/onc.2008.245 (2008).

45 Gu, H. & Neel, B. G. The GAB in signal transduction. *Trends in Cell Biology* 13, 122-130, doi:10.1016/s0962-8924(03)00002-3 (2003).

46 Lazzara, M. J. et al. Impaired SHP2-mediated extracellular signal-regulated kinase activation contributes to gefitinib sensitivity of lung cancer cells with epidermal growth factor receptor-activating mutations. *Cancer Research* 70, 3843-3850, doi:10.1158/0008-5472.can-09-3421 (2010).

47 Furcht, C. M., Munoz Rojas, A. R., Nihalani, D. & Lazzara, M. J. Diminished functional role and altered localization of SHP2 in non-small cell lung cancer cells with EGFR-activating mutations. *Oncogene* 32, 2346-2355, doi:10.1038/onc.2012.240 (2013).

48 Bermudez, O., Marchetti, S., Pages, G. & Gimond, C. Post-translational regulation of the ERK phosphatase DUSP6/MKP3 by the mTOR pathway. *Oncogene* 27, 3685-3691, doi:10.1038/sj.onc.1211040 (2008).

Various features of the invention are set forth in the appended claims.

The invention claimed is:

1. A nanoparticle conjugate comprising a small interfering RNA (siRNA) covalently linked to an antibody that is bonded to the surface of a gelatin nanoparticle that physically encapsulates a drug, wherein one end of siRNA is coupled to an epidermal growth factor receptor (EGFR) targeting monoclonal antibody via a thio-ether bond, and a lysine functional group present on the antibody is bridged with carboxyl groups present on the gelatin nanoparticle.

2. The conjugate of claim 1, wherein the drug comprises a tyrosine kinase inhibitor drug.

3. The conjugate of claim 1, wherein the drug is selected from the group consisting of cisplatin, oxaliplatin, gefitinib, and erlotinib.

4. The conjugate of claim 1, wherein the siRNA is selected from the group consisting of a siRNA specific to mutant KRAS and siRNA specific to AXL.

5. The conjugate of claim 1, wherein the siRNA is specific for KRAS with a point mutation in codon 12.

6. A nanoparticle conjugate comprising a small interfering RNA (siRNA) linked to an antibody that is bonded to the surface of a gelatin nanoparticle that physically encapsulates a drug, wherein the siRNA comprises 5'-GUUGGAGCUU-GUGGCGUAGUUUU-3' (SEQ ID NO. 1) annealed with 5'-AACUACGCCACAAGCUCCAACUU-3' (SEQ ID NO. 2).

7. The conjugate of claim 6, wherein 5' guanine in the oligonucleotide with SEQ ID NO. 1 is modified with the disulfide (S—S) moiety.

8. A nanoparticle conjugate comprising a small interfering RNA (siRNA) linked to an antibody that is bonded to the surface of a gelatin nanoparticle that physically encapsulates a drug, wherein the si-RNA comprises 5'- GGAACUG-CAUGCUGAAUGAUU (SEQ ID NO. 3) annealed with 5'-UCAUUCAGCAUGCAGUUCCUU-3' (SEQ ID NO. 4).

9. The conjugate of claim 8, wherein 5' guanine in the oligonucleotide with SEQ ID NO. 3 is modified with the disulfide (S—S) moiety.

10. The conjugate of claim 1, wherein the gelatin particle is prepared from gelatin 300 bloom by the two-step desolvation process.

* * * * *

SEQUENCE LISTING

<160> NUMBER OF SEQ ID NOS: 4

<210> SEQ ID NO 1
<211> LENGTH: 23
<212> TYPE: RNA
<213> ORGANISM: Artificial Sequence
<220> FEATURE:
<223> OTHER INFORMATION: Oligonucleotide synthesized in laboratory

<400> SEQUENCE: 1
guuggagcuu guggcguagu uuu                                           23

<210> SEQ ID NO 2
<211> LENGTH: 23
<212> TYPE: RNA

```
<213> ORGANISM: Artificial Sequence
<220> FEATURE:
<223> OTHER INFORMATION: Oligonucleotide synthesized in laboratory

<400> SEQUENCE: 2
aacuacgcca caagcuccaa cuu                                              23

<210> SEQ ID NO 3
<211> LENGTH: 21
<212> TYPE: RNA
<213> ORGANISM: Artificial Sequence
<220> FEATURE:
<223> OTHER INFORMATION: Oligonucleotide synthesized in laboratory

<400> SEQUENCE: 3
ggaacugcau gcugaaugau u                                                21

<210> SEQ ID NO 4
<211> LENGTH: 21
<212> TYPE: RNA
<213> ORGANISM: Artificial Sequence
<220> FEATURE:
<223> OTHER INFORMATION: Oligonucleotide synthesized in laboratory

<400> SEQUENCE: 4
ucauucagca ugcaguuccu u                                                21
```